(12) United States Patent
Crofts et al.

(10) Patent No.: US 6,998,473 B1
(45) Date of Patent: Feb. 14, 2006

(54) ISOFORMS OF THE HUMAN VITAMIN D RECEPTOR

(75) Inventors: Linda Anne Crofts, Etskineville (AU); Manuela S. Hancock, Victoria (AU); Nigel A. Morrison, Sorrento (AU); John A. Eisman, Paddington (AU)

(73) Assignee: Garvan Institute of Medical Research, Darlinghurst (AU)

( * ) Notice: Subject to any disclaimer, the term of this patent is extended or adjusted under 35 U.S.C. 154(b) by 0 days.

(21) Appl. No.: 09/509,482

(22) PCT Filed: Sep. 29, 1998

(86) PCT No.: PCT/AU98/00817

§ 371 (c)(1),
(2), (4) Date: Sep. 15, 2000

(87) PCT Pub. No.: WO99/16872

PCT Pub. Date: Apr. 8, 1999

(30) Foreign Application Priority Data

Sep. 29, 1997 (AU) .................................. PO9500

(51) Int. Cl.
C12N 15/12 (2006.01)

(52) U.S. Cl. ................. 536/23.5; 435/69.1; 435/252.3; 435/320.1; 536/24.3

(58) Field of Classification Search ............... 435/69.1, 435/252.3, 320.1; 536/23.5
See application file for complete search history.

(56) References Cited

OTHER PUBLICATIONS

MacDonald et al. Baculovirus-mediated Expression of the Human Vitamine D Receptor, Oct. 5, 1991, J. Biol. Chem. 266(28):18808-18813.*
Cretin et al. The phosphoenolpyruvate carboxylase gene family of Sorghum: promoter structures, amino acid sequences and expression of genes. 1991, Gene 99:87-94.*
Whitehead, R. H. et al., "*A New Colon Carcinoma Cell Line (LIM1863) That Grows as Organoids With Spontaneous Differentiation into Crypt-Like Structures in Vitro*", Cancer Research 47; 2683-2689 (May 15, 1987).

Slater, M. et al., "*Modulation of Growth factor Incorporation into ECM of Human Osteoblast-Like Cells in Vitro by 17β-estradiol*", Cancer Research 47; 2683-2689 (May 15, 1987).
Saijo, T. et al., "*A Unique Mutation in the Vitamin D receptor Gene in Three Japanese Patients with Vitamin-D dependent Rickets Type II: Utility of Single-Strand Conformation Polymorphism Analysis for Heterozygous Carrier Detection*", Am. J. Hum. Genet. 49: 668-673 (1991).
Lu, Z. et al., "*Cloning and Origin of the Two forms of Chicken Vitamin D Receptor*", Archives of Biochemistry and Biophysics vol. 339, No. 1; 99-106 (1997).
Ebihara, K. et al., "*Intron Retention Generates A Novel Isoforms of the Murine Vitamin D Receptor That Acts in a Dominant Negative Way on the Vitamin D Signaling Pathway*", Molecular and Cellular Biology: 3393-3400 (1996).
Haussler M. R. et al., "The vitamin D hormone and its nuclear receptor: molecular actions and disease states", Journal of Endocrinology, Bristol, GB, (1997), vol. 154, pp. s57-s73.
Jurutka, et al., "Human D receptor phosphorylation by casein kinase II at ser-208 potentiates transcriptional activation", Proc. Natl. Acad. Sci. USA, (1996), vol. 93, pp. 3519-3524.
Sunn KL, et al., "Novel N-terminal variant of human VDR", Molecular Endocrinology 15 (9): 1599-1609.
Baker, A. R. et al., Proc. Nat. Acad. Sci. USA., 85:3294-3298, 1988.
Goto, H et al., Biochim Biophys Acta., 1132:103-108, 1992.
Miyamoto, K. et al., Mol. Endocrin., 11(8): 1165-1179, 1997.
Crofts, L.A. et al., Proc. Nat. Acad. Sci. USA, 95:10529-10534, 1998.

* cited by examiner

Primary Examiner—John Ulm
(74) Attorney, Agent, or Firm—Carol L. Francis; Bozicevic, Field & Francis LLP

(57) ABSTRACT

The invention provides isolated polynucleotide molecules which encode novel isoforms of the human Vitamin D receptor (hVDR) or variant transcripts for hVDR. These isolated polynucleotide molecules may be utilized in, for example, methods of screening compounds for VDR agonist and/or antagonist activities.

37 Claims, 21 Drawing Sheets

FIG. 1C

Transcript 1:                                                                                              MEAMA ASTSL PDPGD FDRNV PRI [DBD] 427aa (SEQ ID NO.14)
Transcript 6: MEWRN KKRSD WLSMV LRTAG VEEAF GSEVS VRPHR RAPLG STYLP PAPSG MEAMA ASTSL PDPGD FDRNV PRI [DBD] 477aa (SEQ ID NO.16)
Transcript 9:                                         MEW RNKKR SDWLS MVLRT AGVEG MEAMA ASTSL PDPGD FDRNV PRI [DBD] 450aa (SEQ ID NO.15)

FIG. 4

A. 5'...atcccttaagGGCTCCTGAACCTAGCCCAGCTGGACGGAG
AAATGGACTCTAGCCTCCTCTGATAGCCTCATGCCAGGCCC
CGTGCACATTGCTTTGCTTGCCTCCCTCAATCCTCATAGCT
TCTCTTTGGGgtaagtacag...3' (SEQ ID NO: 13)

B. 5'...TGCGACCTTGGCGGTGAGCCTGGGGACAGGGGTGAGGC
CAGAGACGGACGGACGCAGGGGCCCGGCCCAAGGCGAGGG
AGAACAGCGGCACTAAGGCAGAAAGGAAGAGGGCGGTGTG
TTCACCCGCAGCCCAATCCATCACTCAGCAACTCCTAGAC
GCTGGTAGAAAGTTCCTCCGAGGAGCCTGCCATCCAGTCGT
GCGTGCAG...3' (SEQ ID NO: 5)

C. 5'...tgtttttagAGGCAGCATGAAACAGTGGGATGTGCAGAG
AGAAGATCTGGGTCCAGTAGCTCTGACACTCCTCAGCTGT
AGAAACCTTGACAACTCTGCACATCAGTTGTACAATGGAA
CGGTATTTTTTACTCTTCATGTCTGAAAAGGCTATGATAA
AGATCAAgtaagatatt...3' (SEQ ID NO: 6)

D. 5'...GTTTCCTTCTTCTGTCGGGGCGCCTTGGCATGGAGTGG
AGGAATAAGAAAAGGAGCGATTGGCTGTCGATGGTGCTCA
GAACTGCTGGAGTGGAGGgtgtgtaacc...3' (SEQ ID NO:

FIG. 5A

```
Transcript 6
(Sequence Range: 1 to 1463)
              10         20         30         40         50
              *    *     *    *     *    *     *    *     *    *
         GTTTCCTTCT TCTGTCGGGG CGCCTTGGCA TGGAGTGGAG GAATAAGAAA
         CAAAGGAAGA AGACAGCCCC GCGGAACCGT ACCTCACCTC CTTATTCTTT
                                              MetGluTrpArg AsnLysLys>

60         70         80         90        100
              *    *     *    *     *    *     *    *     *    *
         AGGAGCGATT GGCTGTCGAT GGTGCTCAGA ACTGCTGGAG TGGAGGAAGC
         TCCTCGCTAA CCGACAGCTA CCACGAGTCT TGACGACCTC ACCTCCTTCG
         ArgSerAsp TrpLeuSerMet ValLeuArg ThrAlaGly ValGluGluAla>

110        120        130        140        150
              *    *     *    *     *    *     *    *     *    *
         CTTTGGGTCT GAAGTGTCTG TGAGACCTCA CAGAAGAGCA CCCCTGGGCT
         GAAACCCAGA CTTCACAGAC ACTCTGGAGT GTCTTCTCGT GGGGACCCGA
          PheGlySer GluValSer ValArgProHis ArgArgAla ProLeuGly>

160        170        180        190        200
              *    *     *    *     *    *     *    *     *    *
         CCACTTACCT GCCCCCTGCT CCTTCAGGGA TGGAGGCAAT GGCGGCCAGC
         GGTGAATGGA CGGGGGACGA GGAAGTCCCT ACCTCCGTTA CCGCCGGTCG
         SerThrTyrLeu ProProAla ProSerGly MetGluAlaMet AlaAlaSer>

210        220        230        240        250
              *    *     *    *     *    *     *    *     *    *
         ACTTCCCTGC CTGACCCTGG AGACTTTGAC CGGAACGTGC CCCGGATCTG
         TGAAGGGACG GACTGGGACC TCTGAAACTG GCCTTGCACG GGGCCTAGAC
          ThrSerLeu ProAspProGly AspPheAsp ArgAsnVal ProArgIleCys>

260        270        280        290        300
              *    *     *    *     *    *     *    *     *    *
         TGGGGTGTGT GGAGACCGAG CCACTGGCTT TCACTTCAAT GCTATGACCT
         ACCCCACACA CCTCTGGCTC GGTGACCGAA AGTGAAGTTA CGATACTGGA
          GlyValCys GlyAspArg AlaThrGlyPhe HisPheAsn AlaMetThr>

310        320        330        340        350
              *    *     *    *     *    *     *    *     *    *
         GTGAAGGCTG CAAAGGCTTC TTCAGGCGAA GCATGAAGCG GAAGGCACTA
         CACTTCCGAC GTTTCCGAAG AAGTCCGCTT CGTACTTCGC CTTCCGTGAT
         CysGluGlyCys LysGlyPhe PheArgArg SerMetLysArg LysAlaLeu>

360        370        380        390        400
              *    *     *    *     *    *     *    *     *    *
         TTCACCTGCC CCTTCAACGG GGACTGCCGC ATCACCAAGG ACAACCGACG
         AAGTGGACGG GGAAGTTGCC CCTGACGGCG TAGTGGTTCC TGTTGGCTGC
          PheThrCys ProPheAsnGly AspCysArg IleThrLys AspAsnArgArg>
```

FIG. 5B

```
          410         420         430         440         450
           *           *           *           *           *
     CCACTGCCAG  GCCTGCCGGC  TCAAACGCTG  TGTGGACATC  GGCATGATGA
     GGTGACGGTC  CGGACGGCCG  AGTTTGCGAC  ACACCTGTAG  CCGTACTACT
      HisCysGln   AlaCysArg  LeuLysArgCys ValAspIle  GlyMetMet>

460         470         480         490         500
           *           *           *           *           *
     AGGAGTTCAT  TCTGACAGAT  GAGGAAGTGC  AGAGGAAGCG  GGAGATGATC
     TCCTCAAGTA  AGACTGTCTA  CTCCTTCACG  TCTCCTTCGC  CCTCTACTAG
      LysGluPheIle LeuThrAsp GluGluVal  GlnArgLysArg GluMetIle>

510         520         530         540         550
           *           *           *           *           *
     CTGAAGCGGA  AGGAGGAGGA  GGCCTTGAAG  GACAGTCTGC  GGCCCAAGCT
     GACTTCGCCT  TCCTCCTCCT  CCGGAACTTC  CTGTCAGACG  CCGGGTTCGA
       LeuLysArg LysGluGluGlu AlaLeuLys   AspSerLeu ArgProLysLeu>

560         570         580         590         600
           *           *           *           *           *
     GTCTGAGGAG  CAGCAGCGCA  TCATTGCCAT  ACTGCTGGAC  GCCCACCATA
     CAGACTCCTC  GTCGTCGCGT  AGTAACGGTA  TGACGACCTG  CGGGTGGTAT
        SerGluGlu GlnGlnArg  IleIleAlaIle LeuLeuAsp  AlaHisHis>

610         620         630         640         650
           *           *           *           *           *
     AGACCTACGA  CCCCACCTAC  TCCGACTTCT  GCCAGTTCCG  GCCTCCAGTT
     TCTGGATGCT  GGGGTGGATG  AGGCTGAAGA  CGGTCAAGGC  CGGAGGTCAA
      LysThrTyrAsp ProThrTyr  SerAspPhe  CysGlnPheArg ProProVal>

660         670         680         690         700
           *           *           *           *           *
     CGTGTGAATG  ATGGTGGAGG  GAGCCATCCT  TCCAGGCCCA  ACTCCAGACA
     GCACACTTAC  TACCACCTCC  CTCGGTAGGA  AGGTCCGGGT  TGAGGTCTGT
      ArgValAsn  AspGlyGlyGly SerHisPro  SerArgPro  AsnSerArgHis>

710         720         730         740         750
           *           *           *           *           *
     CACTCCCAGC  TTCTCTGGGG  ACTCCTCCTC  CTCCTGCTCA  GATCACTGTA
     GTGAGGGTCG  AAGAGACCCC  TGAGGAGGAG  GAGGACGAGT  CTAGTGACAT
       ThrProSer  PheSerGly  AspSerSerSer SerCysSer  AspHisCys>

760         770         780         790         800
           *           *           *           *           *
     TCACCTCTTC  AGACATGATG  GACTCGTCCA  GCTTCTCCAA  TCTGGATCTG
     AGTGGAGAAG  TCTGTACTAC  CTGAGCAGGT  CGAAGAGGTT  AGACCTAGAC
      IleThrSerSer AspMetMet AspSerSer  SerPheSerAsn LeuAspLeu>

810         820         830         840         850
           *           *           *           *           *
     AGTGAAGAAG  ATTCAGATGA  CCCTTCTGTG  ACCCTAGAGC  TGTCCCAGCT
     TCACTTCTTC  TAAGTCTACT  GGGAAGACAC  TGGGATCTCG  ACAGGGTCGA
       SerGluGlu AspSerAspAsp ProSerVal  ThrLeuGlu  LeuSerGlnLeu>
```

FIG. 5C

```
         860        870        880        890        900
          *  *      *  *      *  *      *  *      *  *
       CTCCATGCTG CCCCACCTGG CTGACCTGGT CAGTTACAGC ATCCAAAAGG
       GAGGTACGAC GGGGTGGACC GACTGGACCA GTCAATGTCG TAGGTTTTCC
       SerMetLeu  ProHisLeu  AlaAspLeuVal SerTyrSer IleGlnLys>

910        920        930        940        950
          *  *      *  *      *  *      *  *      *  *
       TCATTGGCTT TGCTAAGATG ATACCAGGAT TCAGAGACCT CACCTCTGAG
       AGTAACCGAA ACGATTCTAC TATGGTCCTA AGTCTCTGGA GTGGAGACTC
       ValIleGlyPhe AlaLysMet IleProGly  PheArgAspLeu ThrSerGlu>

960        970        980        990        1000
          *  *      *  *      *  *      *  *      *  *
       GACCAGATCG TACTGCTGAA GTCAAGTGCC ATTGAGGTCA TCATGTTGCG
       CTGGTCTAGC ATGACGACTT CAGTTCACGG TAACTCCAGT AGTACAACGC
       AspGlnIle  ValLeuLeuLys SerSerAla IleGluVal  IleMetLeuArg>

1010       1020       1030       1040       1050
          *  *      *  *      *  *      *  *      *  *
       CTCCAATGAG TCCTTCACCA TGGACGACAT GTCCTGGACC TGTGGCAACC
       GAGGTTACTC AGGAAGTGGT ACCTGCTGTA CAGGACCTGG ACACCGTTGG
       SerAsnGlu  SerPheThr  MetAspAspMet SerTrpThr CysGlyAsn>

1060       1070       1080       1090       1100
          *  *      *  *      *  *      *  *      *  *
       AAGACTACAA GTACCGCGTC AGTGACGTGA CCAAAGCCGG ACACAGCCTG
       TTCTGATGTT CATGGCGCAG TCACTGCACT GGTTTCGGCC TGTGTCGGAC
       GlnAspTyrLys TyrArgVal SerAspVal  ThrLysAlaGly HisSerLeu>

1110       1120       1130       1140       1150
          *  *      *  *      *  *      *  *      *  *
       GAGCTGATTG AGCCCCTCAT CAAGTTCCAG GTGGGACTGA AGAAGCTGAA
       CTCGACTAAC TCGGGGAGTA GTTCAAGGTC CACCCTGACT TCTTCGACTT
       GluLeuIle  GluProLeuIle LysPheGln ValGlyLeu  LysLysLeuAsn>

1160       1170       1180       1190       1200
          *  *      *  *      *  *      *  *      *  *
       CTTGCATGAG GAGGAGCATG TCCTGCTCAT GGCCATCTGC ATCGTCTCCC
       GAACGTACTC CTCCTCGTAC AGGACGAGTA CCGGTAGACG TAGCAGAGGG
       LeuHisGlu  GluGluHis  ValLeuLeuMet AlaIleCys IleValSer>

1210       1220       1230       1240       1250
          *  *      *  *      *  *      *  *      *  *
       CAGATCGTCC TGGGGTGCAG GACGCCGCGC TGATTGAGGC CATCCAGGAC
       GTCTAGCAGG ACCCCACGTC CTGCGGCGCG ACTAACTCCG GTAGGTCCTG
       ProAspArgPro GlyValGln AspAlaAla  LeuIleGluAla IleGlnAsp>

1260       1270       1280       1290       1300
          *  *      *  *      *  *      *  *      *  *
       CGCCTGTCCA ACACACTGCA GACGTACATC CGCTGCCGCC ACCCGCCCCC
       GCGGACAGGT TGTGTGACGT CTGCATGTAG GCGACGGCGG TGGGCGGGGG
       ArgLeuSer  AsnThrLeuGln ThrTyrIle ArgCysArg  HisProProPro>
```

FIG. 5D

```
         1310       1320       1330       1340       1350
          *  *       *  *       *  *       *  *       *  *
       GGGCAGCCAC CTGCTCTATG CCAAGATGAT CCAGAAGCTA GCCGACCTGC
       CCCGTCGGTG GACGAGATAC GGTTCTACTA GGTCTTCGAT CGGCTGGACG
       GlySerHis  LeuLeuTyr  AlaLysMetIle GlnLysLeu AlaAspLeu>

1360       1370       1380       1390       1400
          *  *       *  *       *  *       *  *       *  *
       GCAGCCTCAA TGAGGAGCAC TCCAAGCAGT ACCGCTGCCT CTCCTTCCAG
       CGTCGGAGTT ACTCCTCGTG AGGTTCGTCA TGGCGACGGA GAGGAAGGTC
       ArgSerLeuAsn GluGluHis SerLysGln  TyrArgCysLeu SerPheGln>

1410       1420       1430       1440       1450
          *  *       *  *       *  *       *  *       *  *
       CCTGAGTGCA GCATGAAGCT AACGCCCCTT GTGCTCGAAG TGTTTGGCAA
       GGACTCACGT CGTACTTCGA TTGCGGGGAA CACGAGCTTC ACAAACCGTT
       ProGluCys  SerMetLysLeu ThrProLeu ValLeuGlu  ValPheGlyAsn>

1460
          *  *
       TGAGATCTCC TGA (SEQ ID NO:2)
       ACTCTAGAGG ACT (SEQ ID NO:17)
       GluIleSer  ***>(SEQ ID NO:9)
```

FIG. 6A

Transcript 9
(Sequence range: 1 to 1382)

```
              10         20         30         40         50
          *    *     *    *     *    *     *    *     *    *
         GTTTCCTTCT TCTGTCGGGG CGCCTTGGCA TGGAGTGGAG GAATAAGAAA
         CAAAGGAAGA AGACAGCCCC GCGGAACCGT ACCTCACCTC CTTATTCTTT
                                          MetGluTrpArg AsnLysLys>

60         70         80         90        100
          *    *     *    *     *    *     *    *     *    *
         AGGAGCGATT GGCTGTCGAT GGTGCTCAGA ACTGCTGGAG TGGAGGGGAT
         TCCTCGCTAA CCGACAGCTA CCACGAGTCT TGACGACCTC ACCTCCCCTA
         ArgSerAsp TrpLeuSerMet ValLeuArg ThrAlaGly ValGluGlyMet>

110        120        130        140        150
          *    *     *    *     *    *     *    *     *    *
         GGAGGCAATG GCGGCCAGCA CTTCCCTGCC TGACCCTGGA GACTTTGACC
         CCTCCGTTAC CGCCGGTCGT GAAGGGACGG ACTGGGACCT CTGAAACTGG
          GluAlaMet AlaAlaSer ThrSerLeuPro AspProGly AspPheAsp>

160        170        180        190        200
          *    *     *    *     *    *     *    *     *    *
         GGAACGTGCC CCGGATCTGT GGGGTGTGTG GAGACCGAGC CACTGGCTTT
         CCTTGCACGG GGCCTAGACA CCCCACACAC CTCTGGCTCG GTGACCGAAA
         ArgAsnValPro ArgIleCys GlyValCys GlyAspArgAla ThrGlyPhe>

210        220        230        240        250
          *    *     *    *     *    *     *    *     *    *
         CACTTCAATG CTATGACCTG TGAAGGCTGC AAAGGCTTCT TCAGGCGAAG
         GTGAAGTTAC GATACTGGAC ACTTCCGACG TTTCCGAAGA AGTCCGCTTC
         HisPheAsn AlaMetThrCys GluGlyCys LysGlyPhe PheArgArgSer>

260        270        280        290        300
          *    *     *    *     *    *     *    *     *    *
         CATGAAGCGG AAGGCACTAT TCACCTGCCC CTTCAACGGG GACTGCCGCA
         GTACTTCGCC TTCCGTGATA AGTGGACGGG GAAGTTGCCC CTGACGGCGT
          MetLysArg LysAlaLeu PheThrCysPro PheAsnGly AspCysArg>

310        320        330        340        350
          *    *     *    *     *    *     *    *     *    *
         TCACCAAGGA CAACCGACGC CACTGCCAGG CCTGCCGGCT CAAACGCTGT
         AGTGGTTCCT GTTGGCTGCG GTGACGGTCC GGACGGCCGA GTTTGCGACA
         IleThrLysAsp AsnArgArg HisCysGln AlaCysArgLeu LysArgCys>

360        370        380        390        400
          *    *     *    *     *    *     *    *     *    *
         GTGGACATCG GCATGATGAA GGAGTTCATT CTGACAGATG AGGAAGTGCA
         CACCTGTAGC CGTACTACTT CCTCAAGTAA GACTGTCTAC TCCTTCACGT
         ValAspIle GlyMetMetLys GluPheIle LeuThrAsp GluGluValGln>
```

FIG. 6B

```
           410         420        430         440        450
            *    *     *    *     *    *      *    *     *    *
         GAGGAAGCGG GAGATGATCC TGAAGCGGAA GGAGGAGGAG GCCTTGAAGG
         CTCCTTCGCC CTCTACTAGG ACTTCGCCTT CCTCCTCCTC CGGAACTTCC
          ArgLysArg  GluMetIle LeuLysArgLys GluGluGlu  AlaLeuLys>

460         470        480         490        500
            *    *     *    *     *    *      *    *     *    *
         ACAGTCTGCG GCCCAAGCTG TCTGAGGAGC AGCAGCGCAT CATTGCCATA
         TGTCAGACGC CGGGTTCGAC AGACTCCTCG TCGTCGCGTA GTAACGGTAT
         AspSerLeuArg ProLysLeu  SerGluGlu GlnGlnArgIle IleAlaIle>

510         520        530         540        550
            *    *     *    *     *    *      *    *     *    *
         CTGCTGGACG CCCACCATAA GACCTACGAC CCCACCTACT CCGACTTCTG
         GACGACCTGC GGGTGGTATT CTGGATGCTG GGGTGGATGA GGCTGAAGAC
          LeuLeuAsp AlaHisHisLys ThrTyrAsp  ProThrTyr SerAspPheCys>

560         570        580         590        600
            *    *     *    *     *    *      *    *     *    *
         CCAGTTCCGG CCTCCAGTTC GTGTGAATGA TGGTGGAGGG AGCCATCCTT
         GGTCAAGGCC GGAGGTCAAG CACACTTACT ACCACCTCCC TCGGTAGGAA
          GlnPheArg  ProProVal ArgValAsnAsp  GlyGlyGly  SerHisPro>

610         620        630         640        650
            *    *     *    *     *    *      *    *     *    *
         CCAGGCCCAA CTCCAGACAC ACTCCCAGCT TCTCTGGGGA CTCCTCCTCC
         GGTCCGGGTT GAGGTCTGTG TGAGGGTCGA AGAGACCCCT GAGGAGGAGG
         SerArgProAsn SerArgHis  ThrProSer PheSerGlyAsp SerSerSer>

660         670        680         690        700
            *    *     *    *     *    *      *    *     *    *
         TCCTGCTCAG ATCACTGTAT CACCTCTTCA GACATGATGG ACTCGTCCAG
         AGGACGAGTC TAGTGACATA GTGGAGAAGT CTGTACTACC TGAGCAGGTC
          SerCysSer AspHisCysIle ThrSerSer  AspMetMet AspSerSerSer>

710         720        730         740        750
            *    *     *    *     *    *      *    *     *    *
         CTTCTCCAAT CTGGATCTGA GTGAAGAAGA TTCAGATGAC CCTTCTGTGA
         GAAGAGGTTA GACCTAGACT CACTTCTTCT AAGTCTACTG GGAAGACACT
          PheSerAsn  LeuAspLeu SerGluGluAsp  SerAspAsp  ProSerVal>

760         770        780         790        800
            *    *     *    *     *    *      *    *     *    *
         CCCTAGAGCT GTCCCAGCTC TCCATGCTGC CCCACCTGGC TGACCTGGTC
         GGGATCTCGA CAGGGTCGAG AGGTACGACG GGGTGGACCG ACTGGACCAG
         ThrLeuGluLeu  SerGlnLeu  SerMetLeu ProHisLeuAla AspLeuVal>

810         820        830         840        850
            *    *     *    *     *    *      *    *     *    *
         AGTTACAGCA TCCAAAAGGT CATTGGCTTT GCTAAGATGA TACCAGGATT
         TCAATGTCGT AGGTTTTCCA GTAACCGAAA CGATTCTACT ATGGTCCTAA
          SerTyrSer IleGlnLysVal  IleGlyPhe  AlaLysMet IleProGlyPhe>
```

FIG. 6C

```
          860        870        880        890        900
           *    *     *    *     *    *     *    *     *    *
      CAGAGACCTC ACCTCTGAGG ACCAGATCGT ACTGCTGAAG TCAAGTGCCA
      GTCTCTGGAG TGGAGACTCC TGGTCTAGCA TGACGACTTC AGTTCACGGT
       ArgAspLeu ThrSerGlu AspGlnIleVal LeuLeuLys SerSerAla>

910        920        930        940        950
           *    *     *    *     *    *     *    *     *    *
      TTGAGGTCAT CATGTTGCGC TCCAATGAGT CCTTCACCAT GGACGACATG
      AACTCCAGTA GTACAACGCG AGGTTACTCA GGAAGTGGTA CCTGCTGTAC
       IleGluValIle MetLeuArg SerAsnGlu SerPheThrMet AspAspMet>

960        970        980        990        1000
           *    *     *    *     *    *     *    *     *    *
      TCCTGGACCT GTGGCAACCA AGACTACAAG TACCGCGTCA GTGACGTGAC
      AGGACCTGGA CACCGTTGGT TCTGATGTTC ATGGCGCAGT CACTGCACTG
       SerTrpThr CysGlyAsnGln AspTyrLys TyrArgVal SerAspValThr>

1010       1020       1030       1040       1050
           *    *     *    *     *    *     *    *     *    *
      CAAAGCCGGA CACAGCCTGG AGCTGATTGA GCCCCTCATC AAGTTCCAGG
      GTTTCGGCCT GTGTCGGACC TCGACTAACT CGGGGAGTAG TTCAAGGTCC
       LysAlaGly HisSerLeu GluLeuIleGlu ProLeuIle LysPheGln>

1060       1070       1080       1090       1100
           *    *     *    *     *    *     *    *     *    *
      TGGGACTGAA GAAGCTGAAC TTGCATGAGG AGGAGCATGT CCTGCTCATG
      ACCCTGACTT CTTCGACTTG AACGTACTCC TCCTCGTACA GGACGAGTAC
       ValGlyLeuLys LysLeuAsn LeuHisGlu GluGluHisVal LeuLeuMet>

1110       1120       1130       1140       1150
           *    *     *    *     *    *     *    *     *    *
      GCCATCTGCA TCGTCTCCCC AGATCGTCCT GGGGTGCAGG ACGCCGCGCT
      CGGTAGACGT AGCAGAGGGG TCTAGCAGGA CCCCACGTCC TGCGGCGCGA
       AlaIleCys IleValSerPro AspArgPro GlyValGln AspAlaAlaLeu>

1160       1170       1180       1190       1200
           *    *     *    *     *    *     *    *     *    *
      GATTGAGGCC ATCCAGGACC GCCTGTCCAA CACACTGCAG ACGTACATCC
      CTAACTCCGG TAGGTCCTGG CGGACAGGTT GTGTGACGTC TGCATGTAGG
       IleGluAla IleGlnAsp ArgLeuSerAsn ThrLeuGln ThrTyrIle>

1210       1220       1230       1240       1250
           *    *     *    *     *    *     *    *     *    *
      GCTGCCGCCA CCCGCCCCCG GCAGCCACC TGCTCTATGC AAGATGATC
      CGACGGCGGT GGGCGGGGGC CGTCGGTGG ACGAGATACG GTTCTACTAG
       ArgCysArgHis ProProPro GlySerHis LeuLeuTyrAla LysMetIle>

1260       1270       1280       1290       1300
           *    *     *    *     *    *     *    *     *    *
      CAGAAGCTAG CCGACCTGCG CAGCCTCAAT GAGGAGCACT CCAAGCAGTA
      GTCTTCGATC GGCTGGACGC GTCGGAGTTA CTCCTCGTGA GGTTCGTCAT
       GlnLysLeu AlaAspLeuArg SerLeuAsn GluGluHis SerLysGlnTyr>
```

FIG. 6D

```
           1310       1320       1330       1340       1350
             *    *    *    *    *    *    *    *    *    *
         CCGCTGCCTC TCCTTCCAGC CTGAGTGCAG CATGAAGCTA ACGCCCCTTG
         GGCGACGGAG AGGAAGGTCG GACTCACGTC GTACTTCGAT TGCGGGGAAC
         ArgCysLeu  SerPheGln  ProGluCysSer MetLysLeu  ThrProLeu>

1360       1370       1380
             *    *    *    *    *    *
         TGCTCGAAGT GTTTGGCAAT GAGATCTCCT GA    (SEQ ID NO:3)
         ACGAGCTTCA CAAACCGTTA CTCTAGAGGA CT    (SEQ ID NO:18)
         ValLeuGluVal PheGlyAsn GluIleSer ***>  (SEQ ID NO:10)
```

FIG. 7A

Transcript 10
(Sequence Range: 1 to 1534)

```
              10         20         30         40         50
           .    *      *    *      *    *      *    *      *    *
         GTTTCCTTCT TCTGTCGGGG CGCCTTGGCA TGGAGTGGAG GAATAAGAAA
         CAAAGGAAGA AGACAGCCCC GCGGAACCGT ACCTCACCTC CTTATTCTTT
                                          MetGluTrpArg AsnLysLys>

60         70         80         90        100
           .    *      *    *      *    *      *    *      *    *
         AGGAGCGATT GGCTGTCGAT GGTGCTCAGA ACTGCTGGAG TGGAGGGGAT
         TCCTCGCTAA CCGACAGCTA CCACGAGTCT TGACGACCTC ACCTCCCCTA
         ArgSerAsp TrpLeuSerMet ValLeuArg ThrAlaGly ValGluGlyMet>

110        120        130        140        150
           .    *      *    *      *    *      *    *      *    *
         GGAGGCAATG GCGGCCAGCA CTTCCCTGCC TGACCCTGGA GACTTTGACC
         CCTCCGTTAC CGCCGGTCGT GAAGGGACGG ACTGGGACCT CTGAAACTGG
          GluAlaMet AlaAlaSer ThrSerLeuPro AspProGly AspPheAsp>

160        170        180        190        200
           .    *      *    *      *    *      *    *      *    *
         GGAACGTGCC CCGGATCTGT GGGGTGTGTG GAGACCGAGC CACTGGCTTT
         CCTTGCACGG GGCCTAGACA CCCCACACAC CTCTGGCTCG GTGACCGAAA
         ArgAsnValPro ArgIleCys GlyValCys GlyAspArgAla ThrGlyPhe>

210        220        230        240        250
           .    *      *    *      *    *      *    *      *    *
         CACTTCAATG CTATGACCTG TGAAGGCTGC AAAGGCTTCT TCAGGTGAGC
         GTGAAGTTAC GATACTGGAC ACTTCCGACG TTTCCGAAGA AGTCCACTCG
         HisPheAsn AlaMetThrCys GluGlyCys LysGlyPhe PheArg*** (SEQ ID NO:11)

260        270        280        290        300
           .    *      *    *      *    *      *    *      *    *
         CCCCCTCCCA GGCTCTCCCC AGTGGAAAGG GAGGGAGAAG AAGCAAGGTG
         GGGGGAGGGT CCGAGAGGGG TCACCTTTCC CTCCCTCTTC TTCGTTCCAC 310        320        330        340        350
           .    *      *    *      *    *      *    *      *    *
         TTTCCATGAA GGGAGCCCTT GCATTTTTCA CATCTCCTTC CTTACAATGT
         AAAGGTACTT CCCTCGGGAA CGTAAAAAGT GTAGAGGAAG GAATGTTACA 360        370        380        390        400
           .    *      *    *      *    *      *    *      *    *
         CCATGGAACA TGCGGCGCTC ACAGCCACAG GAGCAGGAGG GTCTTGGCGA
         GGTACCTTGT ACGCCGCGAG TGTCGGTGTC CTCGTCCTCC CAGAACCGCT
```

FIG. 7B

```
               410        420        430        440        450
                 *  *       *  *       *  *       *  *       *  *
            AGCATGAAGC GGAAGGCACT ATTCACCTGC CCCTTCAACG GGGACTGCCG
            TCGTACTTCG CCTTCCGTGA TAAGTGGACG GGGAAGTTGC CCCTGACGGC 460        470        480        490        500
                 *  *       *  *       *  *       *  *       *  *
            CATCACCAAG GACAACCGAC GCCACTGCCA GGCCTGCCGG CTCAAACGCT
            GTAGTGGTTC CTGTTGGCTG CGGTGACGGT CCGGACGGCC GAGTTTGCGA 510        520        530        540        550
                 *  *       *  *       *  *       *  *       *  *
            GTGTGGACAT CGGCATGATG AAGGAGTTCA TTCTGACAGA TGAGGAAGTG
            CACACCTGTA GCCGTACTAC TTCCTCAAGT AAGACTGTCT ACTCCTTCAC 560        570        580        590        600
                 *  *       *  *       *  *       *  *       *  *
            CAGAGGAAGC GGGAGATGAT CCTGAAGCGG AAGGAGGAGG AGGCCTTGAA
            GTCTCCTTCG CCCTCTACTA GGACTTCGCC TTCCTCCTCC TCCGGAACTT 610        620        630        640        650
                 *  *       *  *       *  *       *  *       *  *
            GGACAGTCTG CGGCCCAAGC TGTCTGAGGA GCAGCAGCGC ATCATTGCCA
            CCTGTCAGAC GCCGGGTTCG ACAGACTCCT CGTCGTCGCG TAGTAACGGT 660        670        680        690        700
                 *  *       *  *       *  *       *  *       *  *
            TACTGCTGGA CGCCCACCAT AAGACCTACG ACCCCACCTA CTCCGACTTC
            ATGACGACCT GCGGGTGGTA TTCTGGATGC TGGGGTGGAT GAGGCTGAAG 710        720        730        740        750
                 *  *       *  *       *  *       *  *       *  *
            TGCCAGTTCC GGCCTCCAGT TCGTGTGAAT GATGGTGGAG GGAGCCATCC
            ACGGTCAAGG CCGGAGGTCA AGCACACTTA CTACCACCTC CCTCGGTAGG 760        770        780        790        800
                 *  *       *  *       *  *       *  *       *  *
            TTCCAGGCCC AACTCCAGAC ACACTCCCAG CTTCTCTGGG GACTCCTCCT
            AAGGTCCGGG TTGAGGTCTG TGTGAGGGTC GAAGAGACCC CTGAGGAGGA 810        820        830        840        850
                 *  *       *  *       *  *       *  *       *  *
            CCTCCTGCTC AGATCACTGT ATCACCTCTT CAGACATGAT GGACTCGTCC
            GGAGGACGAG TCTAGTGACA TAGTGGAGAA GTCTGTACTA CCTGAGCAGG 860        870        880        890        900
                 *  *       *  *       *  *       *  *       *  *
            AGCTTCTCCA ATCTGGATCT GAGTGAAGAA GATTCAGATG ACCCTTCTGT
            TCGAAGAGGT TAGACCTAGA CTCACTTCTT CTAAGTCTAC TGGGAAGACA 910        920        930        940        950
                 *  *       *  *       *  *       *  *       *  *
            GACCCTAGAG CTGTCCCAGC TCTCCATGCT GCCCCACCTG GCTGACCTGG
            CTGGGATCTC GACAGGGTCG AGAGGTACGA CGGGGTGGAC CGACTGGACC
```

FIG. 7C

```
         960        970        980        990       1000
          *  *       *  *       *  *       *  *       *  *
    TCAGTTACAG CATCCAAAAG GTCATTGGCT TTGCTAAGAT GATACCAGGA
    AGTCAATGTC GTAGGTTTTC CAGTAACCGA AACGATTCTA CTATGGTCCT 1010       1020       1030       1040       1050
          *  *       *  *       *  *       *  *       *  *
    TTCAGAGACC TCACCTCTGA GGACCAGATC GTACTGCTGA AGTCAAGTGC
    AAGTCTCTGG AGTGGAGACT CCTGGTCTAG CATGACGACT TCAGTTCACG 1060       1070       1080       1090       1100
          *  *       *  *       *  *       *  *       *  *
    CATTGAGGTC ATCATGTTGC GCTCCAATGA GTCCTTCACC ATGGACGACA
    GTAACTCCAG TAGTACAACG CGAGGTTACT CAGGAAGTGG TACCTGCTGT 1110       1120       1130       1140       1150
          *  *       *  *       *  *       *  *       *  *
    TGTCCTGGAC CTGTGGCAAC CAAGACTACA AGTACCGCGT CAGTGACGTG
    ACAGGACCTG GACACCGTTG GTTCTGATGT TCATGGCGCA GTCACTGCAC 1160       1170       1180       1190       1200
          *  *       *  *       *  *       *  *       *  *
    ACCAAAGCCG GACACAGCCT GGAGCTGATT GAGCCCCTCA TCAAGTTCCA
    TGGTTTCGGC CTGTGTCGGA CCTCGACTAA CTCGGGGAGT AGTTCAAGGT 1210       1220       1230       1240       1250
          *  *       *  *       *  *       *  *       *  *
    GGTGGGACTG AAGAAGCTGA ACTTGCATGA GGAGGAGCAT GTCCTGCTCA
    CCACCCTGAC TTCTTCGACT TGAACGTACT CCTCCTCGTA CAGGACGAGT 1260       1270       1280       1290       1300
          *  *       *  *       *  *       *  *       *  *
    TGGCCATCTG CATCGTCTCC CCAGATCGTC CTGGGGTGCA GGACGCCGCG
    ACCGGTAGAC GTAGCAGAGG GGTCTAGCAG GACCCCACGT CCTGCGGCGC 1310       1320       1330       1340       1350
          *  *       *  *       *  *       *  *       *  *
    CTGATTGAGG CCATCCAGGA CCGCCTGTCC AACACACTGC AGACGTACAT
    GACTAACTCC GGTAGGTCCT GGCGGACAGG TTGTGTGACG TCTGCATGTA 1360       1370       1380       1390       1400
          *  *       *  *       *  *       *  *       *  *
    CCGCTGCCGC CACCCGCCCC CGGGCAGCCA CCTGCTCTAT GCCAAGATGA
    GGCGACGGCG GTGGGCGGGG GCCCGTCGGT GGACGAGATA CGGTTCTACT 1410       1420       1430       1440       1450
          *  *       *  *       *  *       *  *       *  *
    TCCAGAAGCT AGCCGACCTG CGCAGCCTCA ATGAGGAGCA CTCCAAGCAG
    AGGTCTTCGA TCGGCTGGAC GCGTCGGAGT TACTCCTCGT GAGGTTCGTC 1460       1470       1480       1490       1500
          *  *       *  *       *  *       *  *       *  *
    TACCGCTGCC TCTCCTTCCA GCCTGAGTGC AGCATGAAGC TAACGCCCCT
    ATGGCGACGG AGAGGAAGGT CGGACTCACG TCGTACTTCG ATTGCGGGGA
```

FIG. 7D

```
       1510        1520        1530
   *      *      *      *      *      *
TGTGCTCGAA GTGTTTGGCA ATGAGATCTC CTGA (SEQ ID NO:4)
ACACGAGCTT CACAAACCGT TACTCTAGAG GACT (SEQ ID NO:19)
```

FIG. 8A

```
            10         20         30         40         50
             *          *          *          *          *
        TGCGACCTTG GCGGTGAGCC TGGGGACAGG GGTGAGGCCA GAGACGGACG
        ACGCTGGAAC CGCCACTCGG ACCCCTGTCC CCACTCCGGT CTCTGCCTGC 60         70         80         90        100
             *          *          *          *          *
        GACGCAGGGG CCCGGCCCAA GGCGAGGGAG AACAGCGGCA CTAAGGCAGA
        CTGCGTCCCC GGGCCGGGTT CCGCTCCCTC TTGTCGCCGT GATTCCGTCT 110        120        130        140        150
             *          *          *          *          *
        AAGGAAGAGG GCGGTGTGTT CACCCGCAGC CCAATCCATC ACTCAGCAAC
        TTCCTTCTCC CGCCACACAA GTGGGCGTCG GGTTAGGTAG TGAGTCGTTG 160        170        180        190        200
             *          *          *          *          *
        TCCTAGACGC TGGTAGAAAG TTCCTCCGAG GAGCCTGCCA TCCAGTCGTG
        AGGATCTGCG ACCATCTTTC AAGGAGGCTC CTCGGACGGT AGGTCAGCAC 210        220        230        240        250
             *          *          *          *          *
        CGTGCAGAAG CCTTTGGGTC TGAAGTGTCT GTGAGACCTC ACAGAAGAGC
        GCACGTCTTC GGAAACCCAG ACTTCACAGA CACTCTGGAG TGTCTTCTCG 260        270        280        290        300
             *          *          *          *          *
        ACCCCTGGGC TCCACTTACC TGCCCCCTGC TCCTTCAGGG ATGGAGGCAA
        TGGGGACCCG AGGTGAATGG ACGGGGACG  AGGAAGTCCC TACCTCCGTT
                                                    MetGluAla>

310        320        330        340        350
             *          *          *          *          *
        TGGCGGCCAG CACTTCCCTG CCTGACCCTG GAGACTTTGA CCGGAACGTG
        ACCGCCGGTC GTGAAGGGAC GGACTGGGAC CTCTGAAACT GGCCTTGCAC
        MetAlaAlaSer ThrSerLeu ProAspPro GlyAspPheAsp ArgAsnVal>

360        370        380        390        400
             *          *          *          *          *
        CCCCGGATCT GTGGGGTGTG TGGAGACCGA GCCACTGGCT TTCACTTCAA
        GGGGCCTAGA CACCCCACAC ACCTCTGGCT CGGTGACCGA AAGTGAAGTT
        ProArgIle CysGlyValCys GlyAspArg AlaThrGly PheHisPheAsn:

410        420        430        440        450
             *          *          *          *          *
        TGCTATGACC TGTGAAGGCT GCAAAGGCTT CTTCAGGCGA AGCATGAAGC
        ACGATACTGG ACACTTCCGA CGTTTCCGAA GAAGTCCGCT TCGTACTTCG
        AlaMetThr CysGluGly CysLysGlyPhe PheArgArg SerMetLys>

460        470        480        490        500
             *          *          *          *          *
        GGAAGGCACT ATTCACCTGC CCCTTCAACG GGACTGCCG CATCACCAAG
        CCTTCCGTGA TAAGTGGACG GGGAAGTTGC CCCTGACGGC GTAGTGGTTC
        ArgLysAlaLeu PheThrCys ProPheAsn GlyAspCysArg IleThrLys>
```

FIG. 8B

```
            510        520        530        540        550
             *          *          *          *          *
        GACAACCGAC GCCACTGCCA GGCCTGCCGG CTCAAACGCT GTGTGGACAT
        CTGTTGGCTG CGGTGACGGT CCGGACGGCC GAGTTTGCGA CACACCTGTA
        AspAsnArg ArgHisCysGln AlaCysArg LeuLysArg CysValAspIle>

560        570        580        590        600
             *          *          *          *          *
        CGGCATGATG AAGGAGTTCA TTCTGACAGA TGAGGAAGTG CAGAGGAAGC
        GCCGTACTAC TTCCTCAAGT AAGACTGTCT ACTCCTTCAC GTCTCCTTCG
         GlyMetMet LysGluPhe IleLeuThrAsp GluGluVal GlnArgLys>

610        620        630        640        650
             *          *          *          *          *
        GGGAGATGAT CCTGAAGCGG AAGGAGGAGG AGGCCTTGAA GGACAGTCTG
        CCCTCTACTA GGACTTCGCC TTCCTCCTCC TCCGGAACTT CCTGTCAGAC
        ArgGluMetIle LeuLysArg LysGluGlu GluAlaLeuLys AspSerLeu>

660        670        680        690        700
             *          *          *          *          *
        CGGCCCAAGC TGTCTGAGGA GCAGCAGCGC ATCATTGCCA TACTGCTGGA
        GCCGGGTTCG ACAGACTCCT CGTCGTCGCG TAGTAACGGT ATGACGACCT
        ArgProLys LeuSerGluGlu GlnGlnArg IleIleAla IleLeuLeuAsp>

710        720        730        740        750
             *          *          *          *          *
        CGCCCACCAT AAGACCTACG ACCCCACCTA CTCCGACTTC TGCCAGTTCC
        GCGGGTGGTA TTCTGGATGC TGGGGTGGAT GAGGCTGAAG ACGGTCAAGG
         AlaHisHis LysThrTyr AspProThrTyr SerAspPhe CysGlnPhe>

760        770        780        790        800
             *          *          *          *          *
        GGCCTCCAGT TCGTGTGAAT GATGGTGGAG GGAGCCATCC TTCCAGGCCC
        CCGGAGGTCA AGCACACTTA CTACCACCTC CCTCGGTAGG AAGGTCCGGG
        ArgProProVal ArgValAsn AspGlyGly GlySerHisPro SerArgPro>

810        820        830        840        850
             *          *          *          *          *
        AACTCCAGAC ACACTCCCAG CTTCTCTGGG GACTCCTCCT CCTCCTGCTC
        TTGAGGTCTG TGTGAGGGTC GAAGAGACCC CTGAGGAGGA GGAGGACGAG
        AsnSerArg HisThrProSer PheSerGly AspSerSer SerSerCysSer>

860        870        880        890        900
             *          *          *          *          *
        AGATCACTGT ATCACCTCTT CAGACATGAT GGACTCGTCC AGCTTCTCCA
        TCTAGTGACA TAGTGGAGAA GTCTGTACTA CCTGAGCAGG TCGAAGAGGT
         AspHisCys IleThrSer SerAspMetMet AspSerSer SerPheSer>

910        920        930        940        950
             *          *          *          *          *
        ATCTGGATCT GAGTGAAGAA GATTCAGATG ACCCTTCTGT GACCCTAGAG
        TAGACCTAGA CTCACTTCTT CTAAGTCTAC TGGGAAGACA CTGGGATCTC
        AsnLeuAspLeu SerGluGlu AspSerAsp AspProSerVal ThrLeuGlu>

960        970        980        990        1000
             *          *          *          *          *
        CTGTCCCAGC TCTCCATGCT GCCCCACCTG GCTGACCTGG TCAGTTACAG
        GACAGGGTCG AGAGGTACGA CGGGGTGGAC CGACTGGACC AGTCAATGTC
        LeuSerGln LeuSerMetLeu ProHisLeu AlaAspLeu ValSerTyrSer>
```

FIG. 8C

```
        1010        1020        1030        1040        1050
          *           *           *           *           *
     CATCCAAAAG GTCATTGGCT TTGCTAAGAT GATACCAGGA TTCAGAGACC
     GTAGGTTTTC CAGTAACCGA AACGATTCTA CTATGGTCCT AAGTCTCTGG
     IleGlnLys  ValIleGly  PheAlaLysMet IleProGly PheArgAsp>

1060        1070        1080        1090        1100
          *           *           *           *           *
     TCACCTCTGA GGACCAGATC GTACTGCTGA AGTCAAGTGC CATTGAGGTC
     AGTGGAGACT CCTGGTCTAG CATGACGACT TCAGTTCACG GTAACTCCAG
     LeuThrSerGlu AspGlnIle ValLeuLeu  LysSerSerAla IleGluVal>

1110        1120        1130        1140        1150
          *           *           *           *           *
     ATCATGTTGC GCTCCAATGA GTCCTTCACC ATGGACGACA TGTCCTGGAC
     TAGTACAACG CGAGGTTACT CAGGAAGTGG TACCTGCTGT ACAGGACCTG
     IleMetLeu  ArgSerAsnGlu SerPheThr MetAspAsp  MetSerTrpThr>

1160        1170        1180        1190        1200
          *           *           *           *           *
     CTGTGGCAAC CAAGACTACA AGTACCGCGT CAGTGACGTG ACCAAAGCCG
     GACACCGTTG GTTCTGATGT TCATGGCGCA GTCACTGCAC TGGTTTCGGC
     CysGlyAsn  GlnAspTyr  LysTyrArgVal SerAspVal ThrLysAla>

1210        1220        1230        1240        1250
          *           *           *           *           *
     GACACAGCCT GGAGCTGATT GAGCCCCTCA TCAAGTTCCA GGTGGGACTG
     CTGTGTCGGA CCTCGACTAA CTCGGGGAGT AGTTCAAGGT CCACCCTGAC
     GlyHisSerLeu GluLeuIle GluProLeu IleLysPheGln ValGlyLeu>

1260        1270        1280        1290        1300
          *           *           *           *           *
     AAGAAGCTGA ACTTGCATGA GGAGGAGCAT GTCCTGCTCA TGGCCATCTG
     TTCTTCGACT TGAACGTACT CCTCCTCGTA CAGGACGAGT ACCGGTAGAC
     LysLysLeu  AsnLeuHisGlu GluGluHis ValLeuLeu  MetAlaIleCys>

1310        1320        1330        1340        1350
          *           *           *           *           *
     CATCGTCTCC CCAGATCGTC CTGGGGTGCA GGACGCCGCG CTGATTGAGG
     GTAGCAGAGG GGTCTAGCAG GACCCCACGT CCTGCGGCGC GACTAACTCC
     IleValSer  ProAspArg  ProGlyValGln AspAlaAla LeuIleGlu>

1360        1370        1380        1390        1400
          *           *           *           *           *
     CCATCCAGGA CCGCCTGTCC AACACACTGC AGACGTACAT CCGCTGCCGC
     GGTAGGTCCT GGCGGACAGG TTGTGTGACG TCTGCATGTA GGCGACGGCG
     AlaIleGlnAsp ArgLeuSer AsnThrLeu  GlnThrTyrIle ArgCysArg>

1410        1420        1430        1440        1450
          *           *           *           *           *
     CACCCGCCCC CGGGCAGCCA CCTGCTCTAT GCCAAGATGA TCCAGAAGCT
     GTGGGCGGGG GCCCGTCGGT GGACGAGATA CGGTTCTACT AGGTCTTCGA
     HisProPro  ProGlySerHis LeuLeuTyr AlaLysMet  IleGlnLysLeu>

1460        1470        1480        1490        1500
          *           *           *           *           *
     AGCCGACCTG CGCAGCCTCA ATGAGGAGCA CTCCAAGCAG TACCGCTGCC
     TCGGCTGGAC GCGTCGGAGT TACTCCTCGT GAGGTTCGTC ATGGCGACGG
     AlaAspLeu  ArgSerLeu  AsnGluGluHis SerLysGln TyrArgCys>
```

FIG. 8D

```
      1510        1520        1530        1540        1550
         *           *           *           *           *
    TCTCCTTCCA  GCCTGAGTGC  AGCATGAAGC  TAACGCCCCT  TGTGCTCGAA
    AGAGGAAGGT  CGGACTCACG  TCGTACTTCG  ATTGCGGGGA  ACACGAGCTT
    LeuSerPheGln ProGluCys  SerMetLys  LeuThrProLeu ValLeuGlu>

1560        1570
         *           *
    GTGTTTGGCA  ATGAGATCTC  CTGA (SEQ ID NO:7)
    CACAAACCGT  TACTCTAGAG  GACT (SEQ ID NO:20)
    ValPheGly  AsnGluIleSer ***>(SEQ ID NO:12)
```

ISOFORMS OF THE HUMAN VITAMIN D RECEPTOR

FIELD OF THE INVENTION

The present invention relates to isolated polynucleotide molecules which encode novel isoforms of the human Vitamin D receptor (hVDR) or variant transcripts for hVDR. The polynucleotide molecules may be utilised in, for example, methods of screening compounds for VDR agonists and/or antagonists.

BACKGROUND OF THE INVENTION

The active hormonal form of vitamin D, 1,25-dihydroxyvitamin $D_3$ (1.25$(OH)_2D_3$), has a central role in calcium and phosphate homeostasis, and the maintenance of bone. Apart from these calcitropic effects, 1.25-$(OH)_2D_3$ has been shown to play a role in controlling cell growth and differentiation in many target tissues. The effects of 1,25-$(OH)_2D_3$ are mediated by a specific receptor protein, the vitamin D receptor (VDR), a member of the nuclear receptor superfamily of transcriptional regulators which also includes steroid, thyroid and retinoid receptors as well as a growing number of orphan receptors. Upon binding hormone the VDR regulates gene expression by direct interaction with specific sequence elements in the promotor regions of hormone responsive target genes. This transactivation or repression involves multiple interactions with other protein cofactors, heterodimerisation partners and the transcription machinery.

Although a cDNA encoding the human VDR was cloned in 1988 (1), little has been documented characterising the gene structure and pattern of transcription since that time. The regulation of VDR abundance is one potentially important mechanism for modulating 1.25-$(OH)_2D$, responsiveness in target cells. It is also possible that VDR has a role in non-transcriptional pathways, perhaps via localization to a non-nuclear compartment and/or interaction with components of other signalling pathways. However, the question of how VDRs are targetted to different cell types and how they are regulated remains unresolved. There have been many reports in the literature describing translational or transcriptional control of VDR levels, both homologously and heterologously, mostly in non-human systems.

A recent study (2) showed that in the kidney, alternative splicing of human VDR transcripts transcribed from a GC rich promotor generates several transcripts which vary only in their 5' UTRs. The present inventors have now identified further upstream exons of the VDR gene which generate 5' variant transcripts, suggesting that the expression of the VDR gene is regulated by more than one promoter. A subset of these transcripts is expressed in a restricted tissue-specific pattern and further variant transcripts have the potential to encode an N-terminally variant protein. These results may have implications for understanding the actions of 1.25-$(OH)_2D_3$ in different tissues and cell types, and the possibility that N-terminally variant VDR proteins may be produced has implications for altered activities such as transactivation function or subcellular localisation of the receptor protein. Furthermore, these variants, by their level, tissue specificity, subcellular localisation and functional activity, may yield targets for pharmaceutical intervention. The variants may also be useful in screening potential analogs and/or antagonists of vitamin D compounds.

DISCLOSURE OF THE INVENTION

In a first aspect, the invention provides an isolated polynucleotide molecule encoding a human Vitamin D receptor (hVDR) isoform, said polynucleotide molecule comprising a nucleotide sequence which includes sequence that substantially corresponds or is functionally equivalent to that of exon 1d of the human VDR gene.

Exon 1d (referred to as exon 1b in the Australian Provisional Patent Specification No. PO9500) is a 96 bp exon located 296 bp downstream from exon 1a (2). The sequence of exon 1d is:

(SEQ ID NO:1)

5'GTTTCCTTCTTCTGTCGGGGCGCCTTGGCATGGAGTGGAGGAATAAGA

AAAGGAGCGATTGGCTGTCGATGGTGCTCAGAACTGCTGGAGTGGAGG3'

The nucleotide sequence of the polynucleotide molecule of the first aspect of the invention, preferably does not include sequence corresponding to that of exon 1a, exon 1f and/or exon 1e. However, the nucleotide sequence of the polynucleotide molecule of the first aspect of the invention, may or may not include sequence that substantially corresponds or is functionally equivalent to that of exon 1b and/or exon 1c.

Preferably, the polynucleotide molecule of the first aspect comprises a nucleotide sequence which includes;
(i) sequence that substantially corresponds or is functionally equivalent to that of exons 1d, 1c and 2–9 and encodes a VDR isoform of approximately 477 amino acids,
(ii) sequence that substantially corresponds or is functionally equivalent to that of exons 1d and 2–9 and encodes a VDR isoform of approximately 450 amino acids, or
(iii) sequence that substantially corresponds or is functionally equivalent to that of exons 1d and 2–9 and further includes a 152 bp intronic sequence, and encodes a truncated VDR isoform of approximately 72 amino acids.

Most preferably, the polynucleotide molecule of the first aspect of the invention comprises a nucleotide sequence substantially corresponding to that shown as SEQ ID NO: 2, SEQ ID NO: 3 or SEQ ID NO: 4.

In a second aspect, the invention provides an isolated polynucleotide molecule encoding a human Vitamin D receptor (hVDR), said polynucleotide molecule comprising a nucleotide sequence which includes sequence that substantially corresponds to that of exon 1f and/or 1e of the human VDR gene.

Exon 1f is a 207 bp exon located more than 9 kb upstream from exon 1a (2) bp upstream from exon 1c (8). The sequence of exon 1f is:

(SEQ ID NO:5)

5'TGCGACCTTGGCGGTGAGCCTGGGGACAGGGGTGAGGCCAGAGACGGA

CGGACGCAGGGGCCCGGCCCAAGGCGAGGGAGAACAGCGGCACTAAGGCA

GAAAGGAAGAGGGCGGTGTGTTCACCCGCAGCCCAATCCATCACTCAGCA

ACTCCTAGACGCTGGTAGAAAGTTCCTCCGAGGAGCCTGCCATCCAGTCG

TGCGTGCAG3'

Exon 1e is a 157 bp exon located 1826 bp upstream from exon 1a (2). The sequence of exon 1e is:

(SEQ ID NO:6)

5'AGGCAGCATGAAACAGTGGGATGTGCAGAGAGAAGATCTGGGTCCAGT

AGCTCTGACACTCCTCAGCTGTAGAAACCTTGACAACTCTGCACATCAGT

TGTACAATGGAACGGTATTTTTTACTCTTCATGTCTGAAAAGGCTATGAT

AAAGATCAA3'

The nucleotide sequence of the polynucleotide molecule of the second aspect of the invention, preferably does not include sequence corresponding to that of exon 1a, 1d or 1b. However, the nucleotide sequence of the polynucleotide molecule of the second aspect of the invention, may or may not include sequence that substantially corresponds or is functionally equivalent to that of exon 1c.

Preferably, the nucleotide molecule of the second aspect comprises a nucleotide sequence which includes sequence that substantially corresponds or is functionally equivalent to that of exons 1f and 2–9.

Most preferably, the polynucleotide molecule of the first aspect of the invention comprises a nucleotide sequence substantially corresponding to that shown as SEQ ID NO: 7.

The polynucleotide molecule of the first or second aspects may be incorporated into plasmids or expression vectors (including viral vectors), which may then be introduced into suitable host cells (e.g. bacterial, yeast, insect and mammalian host cells). Such host cells may be used to express the VDR or functionally equivalent fragment thereof encoded by the isolated polynucleotide molecule.

Accordingly, in a third aspect, the present invention provides a host cell transformed with the polynucleotide molecule of the first or second aspect.

In a fourth aspect, the present invention provides a method of producing a VDR or a functionally equivalent fragment thereof, comprising culturing the host cell of the first or second aspect under conditions enabling the expression of the polynucleotide molecule and, optionally, recovering the VDR or functionally equivalent fragment thereof.

Preferably, the host cell is of mammalian origin. Preferred examples include NIH 3T3 and COS 7 cells.

In a preferred embodiment, the VDR or functionally equivalent fragment thereof is localised to a cell membrane or other subcellular compartment as distinct from a nuclear localisation.

The polynucleotide molecules of the first aspect of the invention encode novel VDR isoforms which may be of interest both clinically and commercially. By using the polynucleotide molecule of the present invention it is possible to obtain VDR isoform proteins or functionally equivalent fragments thereof in a substantially pure form.

Accordingly, in a fifth aspect, the present invention provides a human VDR isoform or functionally equivalent fragment thereof encoded by a polynucleotide molecule of the first aspect, said VDR isoform or functionally equivalent fragment thereof being in a substantially pure form.

In a sixth aspect, the present invention provides an antibody or antibody fragment capable of specifically binding to the VDR isoform of the fourth aspect.

The antibody may be monoclonal or polyclonal, however, it is presently preferred that the antibody is a monoclonal antibody. Suitable antibody fragments include Fab, F(ab')$_2$ and scFv.

In an eighth aspect, the present invention provides a non-human animal transformed with a polynucleotide molecule according to the first or second aspect of the invention.

In a seventh aspect, the invention provides a method for detecting agonist and/or antagonist compounds of a VDR isoform of the fourth aspect, comprising contacting said VDR isoform, functionally equivalent fragment thereof or a cell transformed with and expressing the polynucleotide molecule of the first aspect, with a test compound under conditions enabling the activation of the VDR isoform or functionally equivalent fragment thereof, and detecting an increase or decrease in the activity of the VDR isoform or functionally equivalent fragment thereof.

An increase or decrease in activity of the receptor or functionally equivalent fragment thereof may be detected by measuring changes in interactions with known cofactors (e.g. SRC-1, GRIP-1 and TFIIB) or unknown cofactors (e.g. through use of the yeast dual hybrid system).

In a ninth aspect, the present invention provides an oligonucleotide or polynucleotide probe comprising a nucleotide sequence of 10 or more nucleotides, the probe comprising a nucleotide sequence such that the probe specifically hybridises to the polynucleotide molecule of the first or second aspect under high stringency conditions (Sambrook et al., *Molecular Cloning: a laboratory manual*, Second Edition, Cold Spring Harbor Laboratory Press).

Preferably, the probe is labelled.

In a tenth aspect, the present invention provides an antisense polynucleotide molecule comprising a nucleotide sequence capable of specifically hybridising to an mRNA molecule which encodes a VDR encoded by the polynucleotide molecule of the first or second aspect, so as to prevent translation of the mRNA molecule.

Such antisense polynucleotide molecules may include a ribozyme region to catalytically inactivate mRNA to which it is hybridised.

The polynucleotide molecule of the first or second aspect of the invention may be a dominant negative mutant which encodes a gene product causing an altered phenotype by, for example, reducing or eliminating the activity of endogenous VDR.

In an eleventh aspect, the invention provides an isolated polynucleotide molecule comprising a nucleotide sequence substantially corresponding or, at least showing >75% (preferably >85% or, even more preferably, >95%) sequence identify to:

(SEQ ID NO:5)

(i) 5'TGCGACCTTGGCGGTGAGCCTGGGGACAGGGGTGAGGCCAGAGA

CGGACGGACGCAGGGGCCCGGCCCAAGGCGAGGGAGAACAGCGGCACTAA

GGCAGAAAGGAAGAGGGCGGTGTGTTCACCCGCAGCCCAATCCATCACTC

AGCAACTCCTAGACGCTGGTAGAAAGTTCCTCCGAGGAGCCTGCCATCCA

GTCGTGCGTGCAG3'(exon 1f), (SEQ ID NO:6)

(ii) 5'AGGCAGCATGAAACAGTGGGATGTGCAGAGAGAAGATCTGGGT

CCAGTAGCTCTGACACTCCTCAGCTGTAGAAACCTTGACAACTCTGCACA

TCAGTTGTACAATGGAACGGTATTTTTTACTCTTCATGTCTGAAAAGGCT

ATGATAAAGATCAA3'(exon 1e), or

-continued (SEQ ID NO:1)

(iii) 5'GTTTCCTTCTTCTGTCGGGGCGCCTTGGCATGGAGTGGAGGA ATAAGAAAAGGAGCGATTGGCTGTCGATGGTGCTCAGAACTGCTGGAGTG GAGG3' (exon 1d).

The polynucleotide molecules of the eleventh aspect may be useful as probes for the detection of VDR variant transcripts and as such may be useful in assessing cell or tissue-specific expression of variant transcripts.

The terms "substantially corresponds" and "substantially corresponding" as used herein in relation to nucleotide sequences is intended to encompass minor variations in the nucleotide sequence which due to degeneracy in the DNA code do not result in a substantial change in the encoded protein. Further, this term is intended to encompass other minor variations in the sequence which may be required to enhance expression in a particular system but in which the variations do not result in a decrease in biological activity of the encoded protein.

The term "functionally equivalent" as used herein in relation to nucleotide sequences encoding a VDR isoform is intended to encompass nucleotide sequence variants of up to 5% sequence divergence (i.e. retaining 95% or more sequence identity) which encode VDR isoforms of substantially equivalent biological activity(ies) as said VDR isoform.

The term "functionally equivalent fragment" as used herein in respect of a VDR isoform is intended to encompass functional peptide and polypeptide fragments of said VDR isoform which include the domain or domains which bestow the biological activity characteristic of said VDR isoform.

The terms "comprise", "comprises" and "comprising" as used throughout the specification are intended to refer to the inclusion of a stated step, component or feature or group of steps, components or features with or without the inclusion of a further step, component or feature or group of steps, components or features.

The invention will hereinafter be further described by way of the following non-limiting example and accompanying figures.

BRIEF DESCRIPTION OF THE FIGURES

FIG. 1C N-terminal variant proteins encoded by novel hVDR transcripts. Transcript 1 corresponds to the published cDNA sequence (1) and encodes the 427-aa hVDR protein. Transcripts 6 and 9 code for a protein with an extra 50 aa or 23 aa, respectively, at the N-terminal. The 23 aa of the hVDR A/B domain are shown in bold.

FIG. 4. Provides the nucleotide sequence of novel exons detected by 5' RACE: (A) exon 1b (SEQ ID NO: 8), (B) exon 1f (SEQ ID NO: 5) [P1f is indicated by an arrow above the sequence], (C) exon 1e (SEQ ID NO: 6), (D) exon 1d (SEQ ID NO: 1) [in-frame ATG codons are highlighted and P1d is indicated by an arrow above the sequence]. Intronic sequences are shown in lower case. Canonical splice site consensus sequences are indicated in bold. The transcription start sites for exons 1f and 1d were determined by the 5 termini of RACE clones. No introit sequence is shown 3' to exon 1f as cosmid clone J5 terminated in the intron between exons 1f and 1e.

FIGS. 5A–5D. Provides the nucleotide sequence corresponding to transcript 6 (see FIG. 1) (SEQ ID NO: 2), together with the predicted amino acid sequence (SEQ ID NO: 9) of the encoded protein. Nucleotides 1–96 correspond to exon 1d; nucleotides 97–1463 correspond to exons 1c to the stop codon in exon 9 (or nucleotides −83–1283 of the hVDR cDNA (1)).

FIGS. 6A–6D. Provides the nucleotide sequence corresponding to transcript 9 (see FIG. 1) (SEQ ID NO: 3), together with the predicted amino acid sequence (SEQ ID NO: 10) of the encoded protein. Nucleotides 1–96 correspond to exon 1d; nucleotides 97–1382 correspond to exon 2 to the stop codon in exon 9 (or nucleotides −2–1283 of the hVDR cDNA (1)).

FIGS. 7A–7D. Provides the nucleotide sequence corresponding to transcript 10 (see FIG. 1) (SEQ ID NO: 4), together with the predicted amino acid sequence (SEQ ID NO: 11) of the encoded protein. Nucleotides 1–96 correspond to exon 1d; nucleotides 97–244 correspond to exon 2; nucleotides 245–396 correspond to intronic sequence immediately 3' to exon 2; nucleotides 397–1534 correspond to exons 3 to the stop codon in exon 9 (or nucleotides 146–1283 of the hVDR cDNA (1)).

FIGS. 8A–8D. Provides the nucleotide sequence corresponding to transcript 11 (see FIG. 1) (SEQ ID NO: 7), together with the predicted amino acid sequence (SEQ ID NO: 12) of the encoded protein. Nucleotides 1–207 correspond to exon 1*f*; nucleotides 208–1574 correspond to exon 1*c* to the stop codon in exon 9 (or nucleotides –83–1283 of the hVDR cDNA (1)).

EXAMPLE

Experimental Procedures

Isolation of Characterisation of Genomic Clones

Figure 1A:
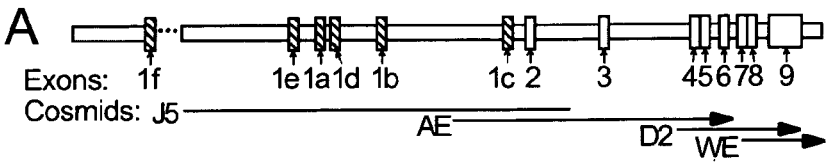
FIG. 1A Human VDR gene locus. Four overlapping cosmid clones were isolated from a human lymphocyte genomic library (Stratagene) and directly sequenced. Clone J5 extends from the 5' flanking region to intron 2; AE, from intron 1b to intron 5; $D_2$, from intron 3 to the 3' UTR; WE, from intron 6 through the 3' flanking region. Sequence upstream of exon 1f was obtained by anchored PCR from genomic DNA.

A human lymphocyte cosmic library (Stratagene, La Jolla, Ca) was screened using a 2.1 kb fragment of the hVDR cDNA encompassing the entire coding region but lacking the 3'UTR, a 241 bp PCR product spanning exons 1 to 3 of the human VDR cDNA, and a 303 bp PCR product spanning exons 3 and 4 of the hVDR cDNA, following standard colony hybridisation techniques. DNA probes were labelled by nick translation (Life Technologies, Gaithersburg, Md.) with $[\alpha^{32}P]$ dCTP. Positively hybridising colonies were picked and secondary and tertiary screens carried out until complete purification. Cosmid DNA from positive clones was purified (Qiagen), digested with different restriction enzymes and characterised by Southern blot analysis using specific [γ32 P]ATP labelled oligonucleotides as probes. Cosmid clones were directly sequenced using dye-termination chemistry and automated fluorescent sequencing on an ABI Prism, 377 DNA Sequencer (Perkin-Elmer, Foster City, Calif.). Sequence upstream of the most 5' cosmid was obtained by anchored PCR from genomic DNA using commercially available anchor ligated DNA (Clontech, Palo Alto, Calif.).

Rapid Amplification of cDNA 5-prime Ends (5'-RACE)

Alternative 5' variants of the human VDR gene were identified by 5'RACE using commercially prepared anchor-ligated cDNA (Clontech) following the instructions of the manufacturer. Two rounds of PCR using nested reverse primers in exons 3 and 2 (P 1: 5'ccgcttcatgcttcgcctgaa-gaagcc-3' (SEQ ID NO: 23), P2: 5'-tgcagaattcacaggtcatag-cattgaag-3' (SEQ ID NO: 24)) were carried out on a Corbett FTS-4000 Capillary Thermal Sequencer (Corbett Research, NSW, Australia). After 26 cycles of PCR, 2% of the primary reaction was reamplified for 31 cycles. The PCR products were cloned into PUC 18 and sequenced by the dideoxy chain termination method.

Cell-Culture

The embryonal kidney cell line, HEK-293, all embryonic intestine cell line, Intestine-407 and WS 1, a foetal skin fibroblast cell line were all cultured in Eagle's MEM with Earle's BSS and supplemented with either 10% heat-inactivated FBS, 15% Y FBS or 10% FBS with non-essential amino acids, respectively. The osteosarcoma cell lines MG-63 and Saos-2 were cultured in Eagle's MEM with nonessential amino acids and 10% heat-inactivated FBS and McCoy's 5a medium with 15% FBS, respectively. The breast carcinoma cell line T47D and the colon carcinoma cell lines LIM 1863 and COLO 206F were cultured in RPMI medium supplemented with 0.2 IU bovine insulin/ml and 10% FBS, 5% FBS or 10% FBS, respectively. LIM 1863 were a gift from R. H. Whitehead (3). HK-2 kidney proximal tubule cells were grown in keratinocyte-serum free medium supplemented with 5 ng/ml recombinant EGF, 40 ug/ml bovine pituitary extract. BC1 foetal osteoblast-like cells were kindly donated by R. Mason (4) and were grown in Eagle's MEM with 5% FBS and 5 mg/L vitamin C. Unless otherwise stated all cell lines were obtained from the American Type Culture Collection (Manassas, Va.).

Reverse Transcripterase-PCR (RT-PCR).

Total RNA extracted from approximately $1.5 \times 10^3$ cells, from leukocytes prepared from 40 ml blood, or from human tissue using acid-phenol extraction was purified by using a guanidium isothiocyanate-cesium chloride step gradient. First-strand cDNA was synthesized from 5 Tg of total RNA primed with random hexamers (Promega) using Superscript II reverse transcriptase (Life Technologies). One-tenth of the cDNA (2TI) was used for subsequent PCR, with 36 cycles of amplification, using exon-specific forward primers (exon 1*a*: corresponding to nucleotides 1–21 of hVDR cDNA (1);
    exon 1*d*: 5'-GGCTGTCGATGGTGCTCAGAAC-3' (SEQ ID NO: 25);
    exon 1*f*: 5'-AAGTTCCTCCGAGGAGCCTGCC-3' (SEQ ID NO: 26));
    and a common reverse primer in exon 3 [corresponding to nucleotides 301–280 of hVDR cDNA (1)]. All RT-PCRs were repeated multiple times by using RNA/cDNA prepared at different times from multiple sources. Each PCR included an appropriate cDNA-negative control, and additional controls included RT-negative controls prepared alongside cDNA and RNA/cDNA prepared from VDR-negative cell lines. PCR products were separated on 2% agarose and visualized with ethidium bromide staining.

Functional Analysis of hVDR Gene Promoters.

Sequences flanking exons 1*a*, 1*d*, and 1*f* (see FIG. 1A) were PCR-amplified by using Pfu polymerase (Stratagene) and cloned into the pGL3 basic vector (Promega) upstream of the luciferase gene reporter. Promoter-reporter constructs were transfected into NIH 3T3 and COS 7 cells by using the standard calcium phosphate-precipitation method, Cells were seeded at $2.3 \pm 2.5 \times 10^6$ per 150-cm$^2$ flask the day before transfection. Several hours before the precipitates were added the medium was changed to DMEM with 2% charcoal-stripped FBS. Cells were exposed to precipitate for 16 h before subculturing and were harvested 24 h later. The parent vector pGL3 basic was used as a promoterless control in these experiments and a simian virus 40 promoter-chloramphenicol acetyltransferase (CAT) gene reporter construct was cotransfected as an internal control for transfection efficiency in each case. The activity of each construct was corrected for transfection efficiency and for the activity of the pGL3 basic empty vector control and expressed as a percentage of the activity of the construct 1*a* (−488,+75). Luciferase and CAT assays were carried out in triplicate, and each construct was tested in transfection at least three times.

Results

Identification of Alternative 5' Variants of the hVDR Gene.

Figure 1B:
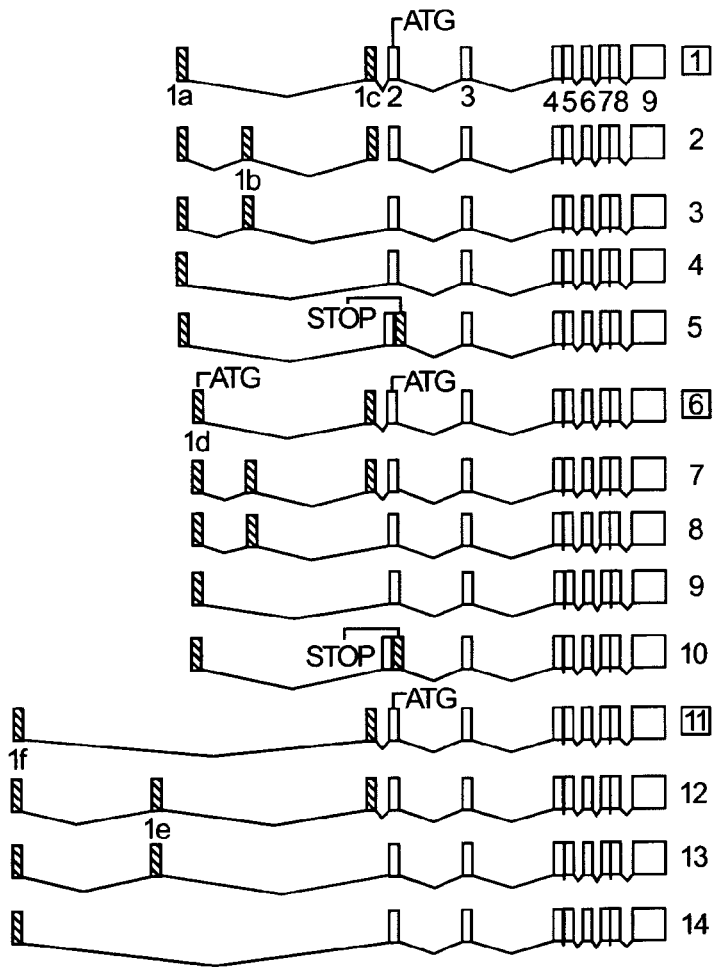
FIG. 1B Structure of hVDR transcripts. Transcripts 1–5 originate from exon 1a. Transcript 1 corresponds to the published cDNA (1). Transcripts 6–10 originate from exon 1d and transcripts 11–14 originate from exon 1f. Boxed numbers indicate the major transcript (based on the relative intensities of the multiple PCR products) within each exon-specific group of transcripts generated with a single primer set. While all transcripts have a translation initiation codon in exon 2, exon 1d transcripts have the potential to initiate translation upstream in exon 1d, with transcripts 6 and 9 encoding VDR proteins with extended N termini.

Upstream exons were identified in human kidney VDR transcripts by 5' RACE (exons 1*f*, 1*e*, 1*d*, and 1*b*) and localized by sequencing of cosmid clones (FIG. 1A). To verify these results and to characterize the structure of the 5' end of the VDR gene, exon-specific forward primers were used with a common reverse primer in exon 3 to amplify specific VDR transcripts from human tissue and cell line RNA (FIG. 1B). The identity of these PCR products was verified by Southern blot and by cloning and sequencing. Five different VDR transcripts originating from exon 1*a* were identified. The major transcript (transcript 1 in FIG.

1B) corresponds to the published cDNA sequence (1). Three less-abundant forms (2, 3, and 4 in FIG. 1B) arise from alternative splicing of exon 1c and a novel 122-bp exon 1b into or out of the final transcript. These three variant transcripts were described recently by Pike and colleagues (2). A fifth minor variant was identified (5 in FIG. 1B) that lacks exons 1b and 1c, but includes an extra 152 bp of intronic sequence immediately 3' to exon 2, potentially encoding a truncated protein as a result of an in-frame termination codon in intron 2.

Four more transcripts were characterized that originate from exon 1f, a novel 207-bp exon more than 9 kb upstream from exon 1a. The major 1f-containing transcript (11 in FIG. 1B) consists of exon 1f spliced immediately adjacent to exon 1c. Three less-abundant variants (12, 13, and 14 in FIG. 1B) arise from alternative splicing of exon 1c and a novel 159-bp exon 1e into or out of the final transcript. All these hVDR variants differ only in their 5' UTRs and encode identical proteins from translation initiation in exon 2.

Of considerable interest, another five hVDR transcripts were identified that originate from exon 1d, a novel 96-bp exon located 296 bp downstream from exon 1a. The major exon 1d-containing transcript (6 in FIG. 1B) utilizes exon 1d in place of exon 1a of the hVDR cDNA. Three minor variants (7, 8, and 9 in FIG. 1B) arise from alternative splicing of exons 1b and 1c into or out of the transcript, analogous to the exon 1a-containing variants 2, 3, and 4. A fifth minor variant transcript (10 in FIG. 1B) lacks exons 1b and 1c, but includes 152 bp of intron 2 analogous to the exon 1a-containing transcript 5, and also potentially encodes a truncated protein. Two of these exon 1d-containing hVDR transcripts encode an N-terminal variant form of the hVDR protein. Utilization of an ATG codon in exon 1d, which is in a favorable context and in-frame with the major translation start site in exon 2, would generate a protein with an additional 50 aa N-terminal to the ATG codon in exon 2 in the case of variant 6 or 23 aa in the case of variant 9 (FIG. 1C).

The relative level of expression of the different transcripts is difficult to address with PCR since relatively minor transcripts may be amplified. However, Southern blots of PCR products from the linear range of PCR amplification indicated that equivalent amounts of PCR product were accumulated after 26 cycles for exon 1a transcripts compared with 30 cycles for exon 1d transcripts, suggesting that 1d abundance is about 5% of that of 1a transcripts. This is consistent with the frequency of clones selected and sequenced from RACE analysis of two separate samples of kidney RNA: 1a (21/27;78%), 1d (2/27; 7%), and 1f (4/27; 15%). RT-PCR with exon 1a-, 1d-, or 1f-specific forward primers and reverse primers in exons 7 or 9, followed by cloning and sequencing, suggests that these 5' variant transcripts are not associated with differences at the 3' end of the transcript.

Exon-Intron Organization of the hVDR Gene.

Overlapping cosmid clones were isolated from a human lymphocyte genomic library and characterized by hybridization to exon-specific oligonucleotide probes (FIG. 1A). The exon-intron boundaries of the hVDR gene were determined by comparison of the genomic sequence from cosmid clones with the cDNA sequence. Upstream exons were localized in the VDR gene by sequencing cosmid clones, which extend approximately 7 kb into the intron between exons 1e and 1f, enabling verification of both their sequence and the presence of consensus splice donor/acceptor sites. Sequence upstream of exon 1f was obtained by anchored PCR from genomic DNA by using commercially available anchor-ligated DNA (CLONTECH). In total, the hVDR gene spans more than 60 kb and consists of at least 14 exons (FIG. 1A).

Tissue-Specific Expression of hVDR Transcripts

Figure 2:
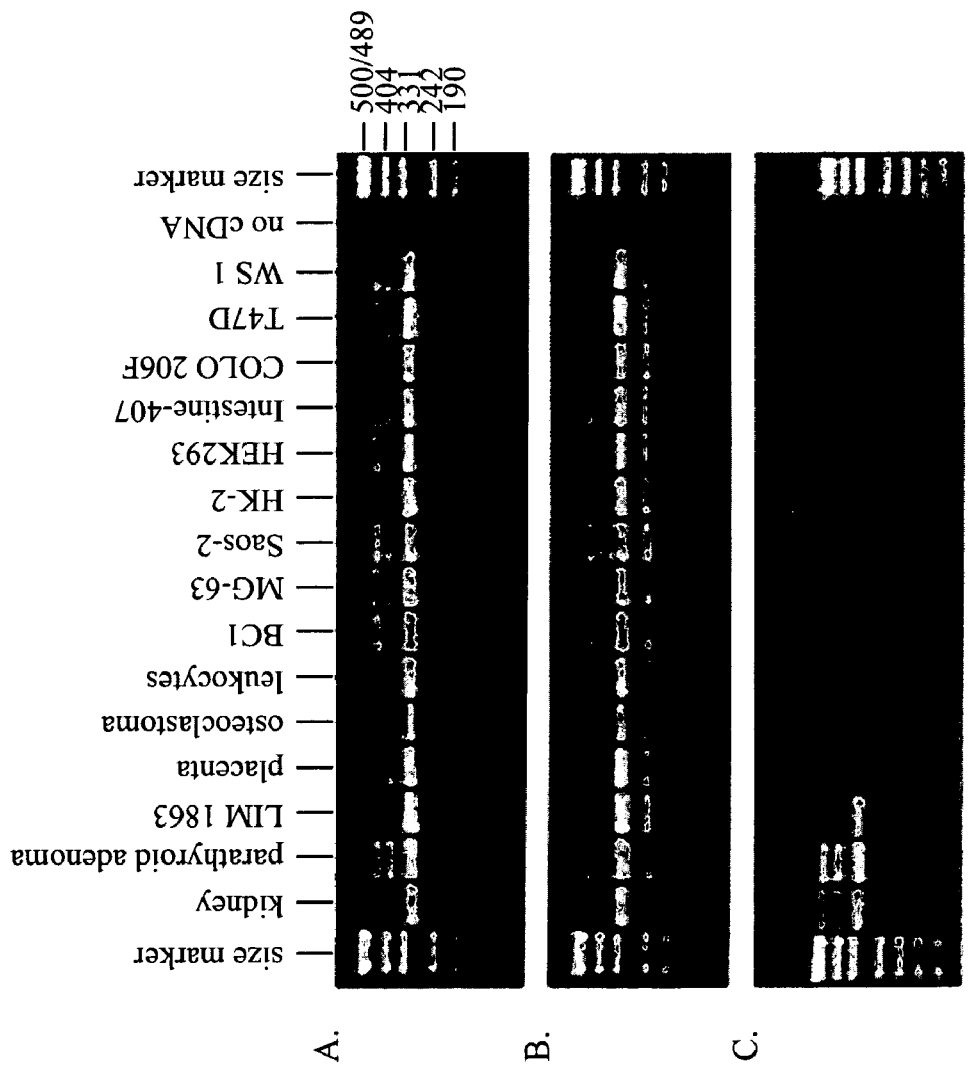
FIG. 2. RT-PCR analysis of expression of variant hVDR transcripts. (A) Exon 1d transcripts (220 bp, 301 bp, 342 bp, 372 bp, and 423 bp). (B) Exon 1d transcripts (224 bp, 305 bp, 346 bp, 376 bp, and 427 bp). (C) Exon 1f transcripts (228 bp, 309 bp, 387 bp, and 468 bp). RT-PCR was carried out with exon 1a-, 1d-, or 1f-specific forward primers and a common reverse primer in exon 3. The sizes of the PCR products and the pattern of bands are similar in A and B by virtue of the identical splicing pattern of exon 1a and 1d transcripts and the fact that primers were designed to generate PCR products of comparable sizes. All tissues and cell lines are human in origin.
Figure 3:
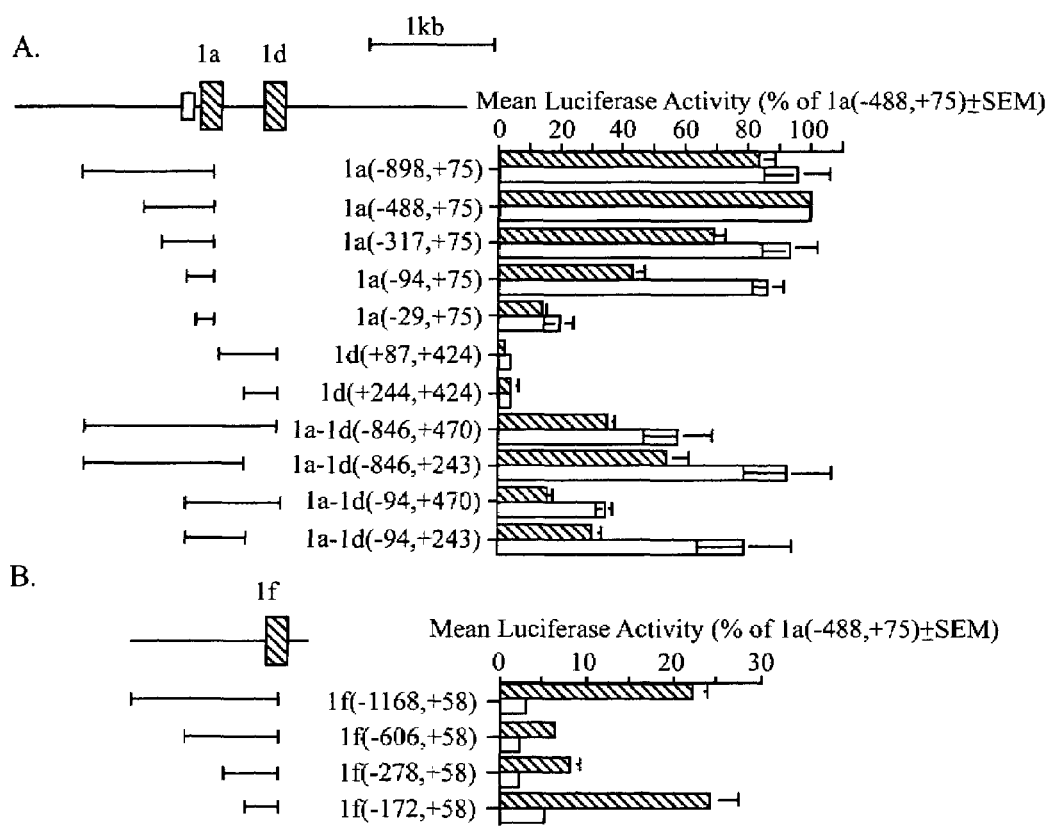
FIG. 3. Functional analysis of sequence-flanking exons 1a and 1d (A) and exon 1f (B) in NIH 3T3 (solid bars) and COS 7 cells (open bars). The parent vector pGL3 basic was used as a promotorless control, and a promoter-chloramphenicol acetyltransferase (CAT) gene reporter construct was cotransfected as an internal control for transfection efficiency in each case. The activity of each construct was corrected for transfection efficiency and for the activity of the pGL3 basic empty vector control and expressed as a percentage of the activity of the construct 1a (−488,+75) SEM of at least three separate transfections. Exon 1a and 1d flanking constructs are defined in relation to the transcription start site of exon 1a, designated 11, which lies 54 nt upstream of the published cDNA (1). Exon 1f flanking constructs are defined relative to the exon 1f transcription start site, designated 11. Transcription start sites were determined by the 5' termini of the longest RACE clones. The open box corresponds to the GC-rich region.

The pattern of expression of variant hVDR transcripts was examined by RT-PCR in a variety of cell lines and tissues with exon 1a-, 1d-, or 1f-specific forward primers and a common reverse primer in exon 3. Exon 1a and 1d transcripts (FIG. 1B, variants 1–10) were coordinately expressed in all RNA samples analyzed (FIGS. 2A and B). Exon 1f transcripts (FIG. 1B, variants 11–14), however, were detected only in RNA from human kidney tissue (two separate samples), human parathyroid adenoma tissue, and an intestinal carcinoma cell line. LIM 1863 (FIG. 2C). Interestingly, these represent major target tissues for the calcitropic effects of vitamin D Functional Analysis of hVDR Gene Promoters Promoter activities of the 5' flanking regions of exons 1a, 1d, and 1f were examined in NIH 3T3 and COS 7 cells (FIG. 3). Sequences flanking exon 1a exhibited high promoter activity in both cell lines (FIG. 3A). Maximum luciferase expression of 36- and 54-fold over the empty vector was attained for construct 1a (−488,+75) in NIH 3T3 and COS 7 cells, respectively. This activity could be attributed largely to a GC-rich region containing multiple consensus Sp1-binding motifs lying within 100 bp immediately adjacent to the transcription start site. This region alone, upstream of a luciferase reporter [construct 1a (−94,+75)], accounted for 43% of the maximum activity observed in NIH 3T3 cells and 86% of the maximum observed in COS 7 cells. The removal of this GC-rich region [construct 1a (−29,+75)] reduced luciferase activity to only 13% of the maximum in NIH 3T3 and 19% in COS 7 cells. Despite the fact that VDR transcripts that originated from exon 1d were identified, distinct promoter activity was not associated with sequences within 300 bp of exon 1d [constructs 1d (+87,+424) and 1d (+244,+424)]; rather, the sequence immediately adjacent to exon 1d may contain a suppressor element (FIG. 3A). Construct 1a–1d (−846,+470), spanning the 5' flanking regions of both exons 1a and 1d, resulted in only 42% and 60% of the activity of 1a (−898.+75) in NIH 3T3 and COS 7 cells, whereas the 3' deletion of 227 bp restored luciferase activity to 65% and 97% of the activity of 1a (−898.+75), respectively. Similarly, the 5' truncated construct 1a–1d (−94,+470), spanning the 5' flanking regions of both 1a and 1d, resulted in only 35% and 40%, of the activity of 1a (−94,+75), while a further 3' deletion of 227 bp restored luciferase activity to 69% and 91% of the activity of 1a (−94,+75) in NIH 3T3 and COS 7 cells. It is possible that transcription from exons 1a and 1d is driven by overlapping promoter regions rather than from two distinct promoters, as has been described for the mouse androgen receptor gene.

Sequence upstream of exon 1f showed significant promoter activity in NIH 3T3 cells of 22% of that of the most active construct, 1a (−488, +75), or 9 fold over pGL3 basic [construct 1f (−1168,+58)] (FIG. 3B). A shorter construct [1f (−172,+58)] had similar activity, with evidence of a suppressor element (between nucleotides −278 and +172) able to repress luciferase activity by 70%. Interestingly, the same constructs were not active in COS 7 cells. This cell line-specific activity of exon 1f flanking sequences may reflect a requirement for tissue- or cell-specific protein factors.

Identification of VDR Isoforms in Whole Cell Lysates

The existence of a VDR isoform including exons 1d and 1c has been confirmed in cell lysates from multiple human, monkey, rat and mouse cell lines derived from kidney, intestine, liver and bone, by immunoprecipitation (using the anti-VDR 9A7 rat monoclonal antibody; Affinity Bioreagents Inc., Golden, Colo.) followed by Western blot analysis. The 1d- and 1c-exon-specific antibodies detected the same band in all immunoprecipitations.

Discussion

The present inventors have identified 5' variant transcripts of the hVDR that suggest the existence of alternative promoters. These transcripts may not have been discriminated in previous Northern analyses because of their similarity in size. Transcription initiation from exons 1a or 1f and alternative splicing generate hVDR transcripts that vary in their 5' UTRs but encode the same 427-aa protein. Transcription initiation from exon 1d and alternative splicing generate hVDR transcripts with the potential to encode variant proteins with an additional 50 or 23 aa at the N terminus. There was no evidence that these 5' variants are associated with differences at the 3' end of the transcript. Although isoforms are common in other members of the nuclear receptor superfamily, the only evidence for isoforms of the hVDR is a common polymorphism in the triplet encoding the initiating methionine of the 427-aa form of the VDR that results in initiation of translation at an alternative start codon beginning at the 10th nucleotide down-stream, encoding a protein truncated by 3 aa at the N terminus (5). Similarly, two forms of the avian VDR differing in size by 14 aa, are generated from a single transcript by alternative translation initiation (6), and in the rat a dominant-negative VDR is generated by intron retention (7).

Heterogeneity in the 5' region is a common feature of other nuclear receptor genes. Tissue-specific alternative-promoter usage generates multiple transcripts of the human estrogen receptor a (ERa), the human and rat mineralocorticoid receptors, and the mouse glucocorticoid receptor (GR), which differ in their 5' UTRs but code for identical proteins. However, other members of the nuclear receptor superfamily have multiple, functionally distinct isoforms arising from differential promoter usage and/or alternative splicing. The generation of N-terminal variant protein isoforms has been described for the progesterone receptor (PR), peroxisome proliferator-activated receptor ($PPAR_o$), and the retinoid and thyroid receptors. Some receptor isoforms exhibit differential promoter-specific transactivation activity. The N-terminal A/B regions of many nuclear receptor proteins possess a ligand-independent transactivation function (AF1). An AF1 domain has been demonstrated for the thyroid receptor b1 (TRb1), ER, GR, PR, PPARg, and the retinoid receptors. The activity of the AF1 domain has been shown to vary in both a tissue- and promoter-specific manner. The N-terminal A/B region of nuclear receptors is the least-conserved domain across the family and between receptor subtypes, varying considerably both in length and sequence. The VDR, however, is unusual as its N-terminal A/B region is much shorter than that of other nuclear receptors, with only 23 aa N-terminal to the DNA-binding domain, and deletion of these residues seems to have no effect on VDR function. This region in other receptors is associated with optimal ligand-dependent transactivation and can interact directly with components of the basal transcription complex. Two stretches of basic amino acid residues, RNKKR (SEQ ID NO: 27) and RPHRR (SEQ ID NO: 28), in the predicted amino acid sequences of the variant hVDR N termini (FIG. 1C) resemble nuclear localization signals. An N-terminal variant VDR protein therefore might exhibit different transactivation potential, possibly mediated by different protein interactions, or may specify a different subcellular localization. The tissue-specific expression of exon 1f-containing transcripts is mediated by a distal promoter more than 9 kb upstream of exons 1a and 1d. Exon 1f transcripts were detected only in kidney tissue, parathyroid adenoma tissue, and an intestinal cell line, LIM 1863. It is interesting that these tissues represent major target tissues for the calcitropic effects of vitamin D. The absence of 1f-containing transcripts in two other kidney cell lines, HK-2 (proximal tubule) and HEK-293 (embryonal kidney), as well as one other embryonal intestinal cell line, Intestine-407, suggests that the expression of 1f transcripts is cell type-specific. The cell line-specific activity of exon 1f flanking sequences in promoter reporter assays may reflect a requirement for tissue- or cell-specific protein factors to mediate expression from this promoter.

This study has demonstrated that expression of the human VDR gene, which spans more than 60 kb and consists of 14 exons, is under complex transcriptional control by multiple promoters. The expression of multiple exon 1f transcripts is mediated by utilization of a distal tissue-specific promoter. Transcription from a proximal promoter, or promoters, generates multiple variant hVDR transcripts, two of which code for N-terminal variant proteins. Multiple, functionally distinct isoforms mediate the tissue- and/or developmental-specific effects of many members of the nuclear receptor superfamily. Although the actual relative abundance of the various transcripts and their levels of translation in vivo have not yet been characterized, the results suggest that major variant isoforms of the hVDR exist. Differential regulation of these hVDR gene promoters and of alternative splicing of variant VDR transcripts may have implications for understanding the various actions of $1,25-(OH)_2D_3$ in different cell types, and variant VDR transcripts may play a role in tissue specific VDR actions in bone and calcium homeostasis.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Baker, A. R. et. al. (1988) Proc. Natl. Acad. Sci. USA 85, 3294–3298
2. Miyamoto, K. et. al. (1997) Mol. Endocrinol. 11, 1165–1179
3. Whitehead, R. H. et. al. (1987) Cancer Res. 47, 2683–2689
4. Slater, M. et al. (1994) Am. J. Physiology 267, E990-1001
5. Saijo, T. et. al. (1991) Amj. Hum. Genet. 49, 668–673
6. Lu, Z. et. al. (1997) Arch. Biochem. Biophys. 339.99–106
7. Ebihara, K. et. al. (1996) Mol. Cell. Biol. 16, 3393–3400

We claim:

1. An isolated polynucleotide molecule comprising:
   a nucleotide sequence encoding exon 1d of the human vitamin D receptor (VDR) gene, or a complement thereof.

2. A polynucleotide molecule according to claim 1, wherein said nucleotide sequence further comprises:
   i) a nucleotide sequence encoding an amino acid sequence of exon 1b, or a complement thereof;
   ii) a nucleotide sequence encoding an amino acid sequence of exon 1c, or a complement thereof; or
   iii) a nucleotide sequence comprising i) and ii).

3. A polynucleotide molecule according to claim 1, wherein the nucleotide sequence includes, from 5' to 3':
   (i) a sequence encoding an amino acid sequence of exons 1d, 1c and 2–9 so as to encode a VDR isoform of approximately 477 amino acids, or a complement thereof;
   (ii) a sequence encoding an amino acid sequence of exons 1d and 2–9 so as to encode a VDR isoform of approximately 450 amino acids, or a complement thereof; or
   (iii) a sequence encoding an amino acid sequence of exons 1d and 2–9 and further includes a 152 bp intronic sequence so as to encode a truncated VDR isoform of approximately 72 amino acids, or a complement thereof.

4. A polynucleotide molecule according to claim 1, wherein the polynucleotide comprises a nucleotide sequence encoding an amino acid sequence encoded by SEQ ID NO:2, SEQ ID NO:3 or SEQ ID NO:4, or a complementary sequence thereof.

5. A plasmid or expression vector comprising a polynucleotide molecule according to claim 1.

6. A host cell transformed with a polynucleotide molecule according to claim 1 or a plasmid or expression vector according to claim 5.

7. A host cell according to claim 6, wherein the cell is a mammalian cell.

8. A host cell according to claim 6, wherein the cell is a NIH 3T3 or COS 7 cell.

9. A method of producing a polypeptide comprising exon 1d of a human vitamin D receptor (VDR), the method comprising:
   culturing a host cell of claim 6, wherein said polynucleotide molecule encodes a polypeptide comprising exon 1d of a human VDR, said culturing being under conditions enabling the expression of the polynucleotide molecule to produce a polypeptide and, optionally, recovering the polypeptide.

10. A method according to claim 9, wherein the polypeptide is expressed onto the host cell membrane or a subcellular compartment.

11. An oligonucleotide or polynucleotide probe comprising a nucleotide sequence having greater than 75% sequence identity to a polynucleotide encoding MEWRNKKRSDWLSMVLRTAGVE (SEQ ID NO:21), or a complement thereof.

12. An antisense polynucleotide molecule comprising a nucleotide sequence having greater than 75% sequence identity to a complement of a polynucleotide encoding MEWRNKKRSDWLSMVLRTAGVE (SEQ ID NO:21).

13. An isolated polynucleotide molecule comprising a nucleotide sequence having greater than 75% sequence identity to a polynucleotide encoding MEWRNKKRSDWLSMVLRTAGVE (SEQ ID NO:21), or a complement thereof.

14. A polynucleotide molecule according to claim 13, wherein said nucleotide sequence further comprises:
  i) a nucleotide sequence encoding an amino acid sequence of exon 1b of the human vitamin D receptor (VDR) isoform, or a complement thereof;
  ii) a nucleotide sequence encoding an amino acid sequence of exon 1c of the human VDR isoform, or a complement thereof; or
  iii) a nucleotide sequence comprising i) and ii).

15. A polynucleotide molecule according to claim 13, wherein the nucleotide sequence comprises, from 5' to 3':
  (i) a sequence encoding an amino acid sequence of exons 1d, 1c and 2–9 of the human vitamin D receptor (VDR) isoform so as to encode a VDR isoform of approximately 477 amino acids, or a complement thereof,
  (ii) a sequence encoding an amino acid sequence of exons 1d and 2–9 or the human VDR isoform so as to encode a VDR isoform of approximately 450 amino acids, or a complement thereof, or
  (iii) a sequence encoding an amino acid sequence of exons 1d and 2–9 of the human VDR isoform and further includes a 152 bp intronic sequence so as to encode a truncated VDR isoform of approximately 72 amino acids, or a complement thereof.

16. An isolated polynucleotide molecule comprising a nucleotide sequence having greater than 85% sequence identity to a polynucleotide encoding MEWRNKKRSDWLSMVLRTAGVE (SEQ ID NO:21), or a complement thereof.

17. An isolated polynucleotide molecule comprising a nucleotide sequence having greater than 95% sequence identity to a polynucleotide encoding MEWRNKKRSDWLSMVLRTAGVE (SEQ ID NO:21), or a complement thereof.

18. An isolated polynucleotide molecule comprising a nucleotide sequence of
5'         GTTTCCTTCTTCTGTCGGGGCGCCTTG-GCATGGAGTGGAGGAATAAGAAAAGGAGCGATTGGCTGTCGATGGTGCTCAGAACT-GCTGGAGTGGAGG3' (SEQ ID NO:1), or a complement thereof.

19. A polynucleotide molecule according to claim 16, 17, or 18, wherein said nucleotide sequence further comprises:
  i) a nucleotide sequence encoding an amino acid sequence of exon 1b of the human vitamin D receptor (VDR) isoform, or a complement thereof;
  ii) a nucleotide sequence encoding an amino acid sequence of exon 1c of the human VDR isoform, or a complement thereof; or
  iii) a nucleotide sequence comprising i) and ii).

20. A polynucleotide molecule according to claim 16, 17, or 18, wherein the nucleotide sequence comprises, from 5' to 3':
  (i) a sequence encoding an amino acid sequence of exons 1d, 1c and 2–9 of the human vitamin D receptor (VDR) isoform so as to encode a VDR isoform of approximately 477 amino acids, or a complement thereof,
  (ii) a sequence encoding an amino acid sequence of exons 1d and 2–9 or the human VDR isoform so as to encode a VDR isoform of approximately 450 amino acids, or a complement thereof, or
  (iii) a sequence encoding an amino acid sequence of exons 1d and 2–9 of the human VDR isoform and further includes a 152 bp intronic sequence so as to encode a truncated VDR isoform of approximately 72 amino acids, or a complement thereof.

21. An isolated polynucleotide molecule comprising a nucleotide sequence of nucleotide residues 30–95 of SEQ ID NO: 1, or a complement thereof.

22. An isolated polynucleotide molecule comprising a nucleotide sequence encoding a human vitamin D receptor (hVDR) isoform comprising the amino acid sequence MEWRNKKRSDWLSMVLRTAGVE (SEQ ID NO:21), or a complement of said nucleotide sequence.

23. A plasmid or expression vector including a polynucleotide molecule according to claim 13, 16, 17, 18, 21 or 22.

24. A recombinant host cell containing a plasmid or expression vector according to claim 23.

25. A host cell according to claim 24, wherein the cell is a mammalian cell.

26. A host cell according to claim 24, wherein the cell is a NIH 3T3 or COS 7 cell.

27. A recombinant host cell containing a polynucleotide molecule according to claim 13, 16, 17, 18, 21 or 22.

28. A method of producing a VDR or VDR isoform polypeptide-comprising
  culturing a host cell comprising a plasmid or expression vector comprising a polynucleotide molecule encoding a human vitamin D receptor (VDR) or VDR isoform, said polynucleotide molecule comprising the nucleotide sequence of a polynucleotide molecule according to claim 18 or 22, said polynucleotide molecule encoding MEWRNKKRSDWLSMVLRTAGVE (SEQ ID NO:21), said culturing being under conditions enabling the expression of the VDR or VDR isoform; and,
  optionally, recovering the VDR or VDR isoform polypeptide.

29. A method according to claim 28, wherein the VDR or VDR isoform polypeptide is expressed onto the host cell membrane or other sub-cellular compartment.

30. An oligonucleotide or polynucleotide probe comprising a nucleotide sequence having greater than 85% sequence identity to a polynucleotide encoding MEWRNKKRSDWLSMVLRTAGVE (SEQ ID NO:21), or a complement thereof.

31. An oligonucleotide or polynucleotide probe comprising a nucleotide sequence having greater than 95% sequence identity to a polynucleotide encoding MEWRNKKRSDWLSMVLRTAGVE (SEQ ID NO:21), or a complement thereof.

32. An oligonucleotide or polynucleotide probe comprising a nucleotide sequence

5'GTTTCCTTCTTCTGTCGGGGCGCCTTG-GCATGGAGTGGAGGAATAAGAAAAGGAGCGATTGGCTGTCGATGGTGCTCAGAACT-GCTGGAGTGGAGG3' (SEQ ID NO:1), or a complement thereof.

33. An oligonucleotide or polynucleotide probe comprising a nucleotide sequence encoding MEWRNKKRSDWLSMVLRTAGVE (SEQ ID NO:21), or a complement thereof.

34. An antisense polynucleotide molecule comprising a nucleotide sequence having greater than 85% sequence identity to a complement of a polynucleotide encoding MEWRNKKRSDWLSMVLRTAGVE (SEQ ID NO:21).

35. An antisense polynucleotide molecule comprising a nucleotide sequence having greater than 95% sequence identity to a complement of a polynucleotide encoding MEWRNKKRSDWLSMVLRTAGVE (SEQ ID NO:21).

36. An antisense polynucleotide molecule a nucleotide sequence complementary to a nucleotide sequence of 5' GTTTCCTTCTTCTGTCGGGGCGCCTTG-GCATGGAGTGGAGGAATAAGAAAAGGAGCGATTGGCTGTCGATGGTGCTCAGAACT-GCTGGAGTGGAGG3' (SEQ ID NO: 1).

37. An antisense polynucleotide molecule comprising a nucleotide sequence complementary to a nucleotide sequence encoding MEWRNKKRSDWLSMVLRTAGVE (SEQ ID NO:21).

* * * * *

SEQUENCE LISTING

<160> NUMBER OF SEQ ID NOS: 28

<210> SEQ ID NO 1
<211> LENGTH: 96
<212> TYPE: DNA
<213> ORGANISM: Homo sapiens

<400> SEQUENCE: 1

```
gtttccttct tctgtcgggg cgccttggca tggagtggag gaataagaaa aggagcgatt    60
ggctgtcgat ggtgctcaga actgctggag tggagg                              96
```

<210> SEQ ID NO 2
<211> LENGTH: 1463
<212> TYPE: DNA
<213> ORGANISM: Homo sapiens

<400> SEQUENCE: 2

```
gtttccttct tctgtcgggg cgccttggca tggagtggag gaataagaaa aggagcgatt    60
ggctgtcgat ggtgctcaga actgctggag tggaggaagc ctttgggtct gaagtgtctg   120
tgagacctca cagaagagca cccctgggct ccacttacct gcccctgct ccttcaggga    180
tggaggcaat ggcggccagc acttccctgc ctgaccctgg agactttgac cggaacgtgc   240
cccggatctg tggggtgtgt ggagaccgag ccactggctt tcacttcaat gctatgacct   300
gtgaaggctg caaaggcttc ttcaggcgaa gcatgaagcg gaaggcacta ttcacctgcc   360
ccttcaacgg ggactgccgc atcaccaagg acaaccgacg ccactgccag gcctgccggc   420
tcaaacgctg tgtggacatc ggcatgatga aggagttcat tctgacagat gaggaagtgc   480
agaggaagcg ggagatgatc ctgaagcgga aggaggagga ggccttgaag gacagtctgc   540
ggcccaagct gtctgaggag cagcagcgca tcattgccat actgctggac gcccaccata   600
agacctacga ccccacctac tccgacttct gccagttccg gcctccagtt cgtgtgaatg   660
atggtggagg gagccatcct tccaggccca ctccagaca cactcccagc ttctctgggg    720
actcctcctc ctcctgctca gatcactgta tcacctcttc agacatgatg gactcgtcca   780
gcttctccaa tctggatctg agtgaagaag attcagatga cccttctgtg acccctagagc   840
tgtcccagct ctccatgctg ccccacctgg ctgacctggt cagttacagc atccaaaagg   900
tcattggctt tgctaagatg ataccaggat tcagagacct cacctctgag gaccagatcg   960
tactgctgaa gtcaagtgcc attgaggtca tcatgttgcg ctccaatgag tccttcacca  1020
tggacgacat gtcctggacc tgtggcaacc aagactacaa gtaccgcgtc agtgacgtga  1080
ccaaagccgg acacagcctg gagctgattg agccctcat caagttccag gtgggactga  1140
agaagctgaa cttgcatgag gaggagcatg tcctgctcat ggccatctgc atcgtctccc  1200
cagatcgtcc tggggtgcag gacgccgcgc tgattgaggc catccaggac cgcctgtcca  1260
acacactgca gacgtacatc cgctgccgcc acccgccccc gggcagccac ctgctctatg  1320
ccaagatgat ccagaagcta gccgacctgc gcagcctcaa tgaggagcac tccaagcagt  1380
accgctgcct ctccttccag cctgagtgca gcatgaagct aacgcccctt gtgctcgaag  1440
tgtttggcaa tgagatctcc tga                                           1463
```

<210> SEQ ID NO 3
<211> LENGTH: 1382
<212> TYPE: DNA
<213> ORGANISM: Homo sapiens

<400> SEQUENCE: 3

```
gtttccttct tctgtcgggg cgccttggca tggagtggag gaataagaaa aggagcgatt      60
ggctgtcgat ggtgctcaga actgctggag tggaggggat ggaggcaatg gcggccagca    120
cttccctgcc tgaccctgga gactttgacc ggaacgtgcc ccggatctgt ggggtgtgtg    180
gagaccgagc cactggcttt cacttcaatg ctatgacctg tgaaggctgc aaaggcttct    240
tcaggcgaag catgaagcgg aaggcactat tcacctgccc cttcaacggg gactgccgca    300
tcaccaagga caaccgacgc cactgccagg cctgccggct caaacgctgt gtggacatcg    360
gcatgatgaa ggagttcatt ctgacagatg aggaagtgca gaggaagcgg agatgatcc    420
tgaagcggaa ggaggaggag gccttgaagg acagtctgcg gcccaagctg tctgaggagc    480
agcagcgcat cattgccata ctgctggacg cccaccataa gacctacgac cccacctact    540
ccgacttctg ccagttccgg cctccagttc gtgtgaatga tggtggaggg agccatcctt    600
ccaggcccaa ctccagacac actcccagct ctctgggga ctcctcctcc tcctgctcag    660
atcactgtat cacctcttca gacatgatgg actcgtccag cttctccaat ctggatctga    720
gtgaagaaga ttcagatgac ccttctgtga ccctagagct gtcccagctc tccatgctgc    780
cccacctggc tgacctggtc agttacagca tccaaaaggt cattggcttt gctaagatga    840
taccaggatt cagagacctc acctctgagg accagatcgt actgctgaag tcaagtgcca    900
ttgaggtcat catgttgcgc tccaatgagt ccttcaccat ggacgacatg tcctggacct    960
gtggcaacca agactacaag taccgcgtca gtgacgtgac caaagccgga cacagcctgg   1020
agctgattga gccctcatc aagttccagg tgggactgaa gaagctgaac ttgcatgagg   1080
aggagcatgt cctgctcatg gccatctgca tcgtctcccc agatcgtcct ggggtgcagg   1140
acgccgcgct gattgaggcc atccaggacc gcctgtccaa cacactgcag acgtacatcc   1200
gctgccgcca cccgccccccg ggcagccacc tgctctatgc caagatgatc cagaagctag   1260
ccgacctgcg cagcctcaat gaggagcact ccaagcagta ccgctgcctc tccttccagc   1320
ctgagtgcag catgaagcta acgccccttg tgctcgaagt gtttggcaat gagatctcct   1380
ga                                                                  1382
```

<210> SEQ ID NO 4
<211> LENGTH: 1534
<212> TYPE: DNA
<213> ORGANISM: Homo sapiens

<400> SEQUENCE: 4

```
gtttccttct tctgtcgggg cgccttggca tggagtggag gaataagaaa aggagcgatt      60
ggctgtcgat ggtgctcaga actgctggag tggaggggat ggaggcaatg gcggccagca    120
cttccctgcc tgaccctgga gactttgacc ggaacgtgcc ccggatctgt ggggtgtgtg    180
gagaccgagc cactggcttt cacttcaatg ctatgacctg tgaaggctgc aaaggcttct    240
tcaggtgagc cccctccca ggctctcccc agtggaaagg gagggagaag aagcaaggtg     300
tttccatgaa gggagcccctt gcatttttca catctccttc cttacaatgt ccatggaaca    360
tgcggcgctc acagccacag gagcaggagg tcttggcga agcatgaagc ggaaggcact    420
attcacctgc cccttcaacg gggactgccg catcaccaag gacaaccgac gccactgcca    480
ggcctgccgg ctcaaacgct gtgtggacat cggcatgatg aaggagttca ttctgacaga    540
tgaggaagtg cagaggaagc gggagatgat cctgaagcgg aaggaggagg aggccttgaa    600
```

| | | | |
|---|---|---|---|
| ggacagtctg | cggcccaagc | tgtctgagga gcagcagcgc | atcattgcca tactgctgga | 660 |
| cgcccaccat | aagacctacg | accccaccta ctccgacttc | tgccagttcc ggcctccagt | 720 |
| tcgtgtgaat | gatggtggag | ggagccatcc ttccaggccc | aactccagac acactcccag | 780 |
| cttctctggg | gactcctcct | cctcctgctc agatcactgt | atcacctctt cagacatgat | 840 |
| ggactcgtcc | agcttctcca | atctggatct gagtgaagaa | gattcagatg acccttctgt | 900 |
| gaccctagag | ctgtcccagc | tctccatgct gccccacctg | gctgacctgg tcagttacag | 960 |
| catccaaaag | gtcattggct | ttgctaagat gataccagga | ttcagagacc tcacctctga | 1020 |
| ggaccagatc | gtactgctga | agtcaagtgc cattgaggtc | atcatgttgc gctccaatga | 1080 |
| gtccttcacc | atggacgaca | tgtcctggac ctgtggcaac | caagactaca agtaccgcgt | 1140 |
| cagtgacgtg | accaaagccg | acacagcctg gagctgatt | gagcccctca tcaagttcca | 1200 |
| ggtgggactg | aagaagctga | acttgcatga ggaggagcat | gtcctgctca tggccatctg | 1260 |
| catcgtctcc | ccagatcgtc | ctggggtgca ggacgccgcg | ctgattgagg ccatccagga | 1320 |
| ccgcctgtcc | aacacactgc | agacgtacat ccgctgccgc | cacccgcccc cgggcagcca | 1380 |
| cctgctctat | gccaagatga | tccagaagct agccgacctg | cgcagcctca atgaggagca | 1440 |
| ctccaagcag | taccgctgcc | tctccttcca gcctgagtgc | agcatgaagc taacgcccct | 1500 |
| tgtgctcgaa | gtgtttggca | atgagatctc ctga | | 1534 |

<210> SEQ ID NO 5
<211> LENGTH: 207
<212> TYPE: DNA
<213> ORGANISM: Homo sapiens

<400> SEQUENCE: 5

| | | | |
|---|---|---|---|
| tgcgaccttg | gcggtgagcc | tggggacagg ggtgaggcca | gagacggacg gacgcagggg | 60 |
| cccggcccaa | ggcgagggag | aacagcggca ctaaggcaga | aaggaagagg gcggtgtgtt | 120 |
| cacccgcagc | ccaatccatc | actcagcaac tcctagacgc | tggtagaaag ttcctccgag | 180 |
| gagcctgcca | tccagtcgtg | cgtgcag | | 207 |

<210> SEQ ID NO 6
<211> LENGTH: 167
<212> TYPE: DNA
<213> ORGANISM: Homo sapiens

<400> SEQUENCE: 6

| | | | |
|---|---|---|---|
| aggcagcatg | aaacagtggg | atgtgcagag agaagatctg | ggtccagtag ctctgacact | 60 |
| cctcagctgt | agaaaccttg | acaactctgc acatcagttg | tacaatggaa cggtatttt | 120 |
| tactcttcat | gtctgaaaag | gctatgataa agatcaagta | agatatt | 167 |

<210> SEQ ID NO 7
<211> LENGTH: 1574
<212> TYPE: DNA
<213> ORGANISM: Homo sapiens

<400> SEQUENCE: 7

| | | | |
|---|---|---|---|
| tgcgaccttg | gcggtgagcc | tggggacagg ggtgaggcca | gagacggacg gacgcagggg | 60 |
| cccggcccaa | ggcgagggag | aacagcggca ctaaggcaga | aaggaagagg gcggtgtgtt | 120 |
| cacccgcagc | ccaatccatc | actcagcaac tcctagacgc | tggtagaaag ttcctccgag | 180 |
| gagcctgcca | tccagtcgtg | cgtgcagaag cctttgggtc | tgaagtgtct gtgagacctc | 240 |
| acagaagagc | cccctgggc | tccacttacc tgcccctgc | tccttcaggg atggaggcaa | 300 |

```
tggcggccag cacttccctg cctgaccctg gagactttga ccggaacgtg ccccggatct    360
gtggggtgtg tggagaccga gccactggct ttcacttcaa tgctatgacc tgtgaaggct    420
gcaaaggctt cttcaggcga agcatgaagc ggaaggcact attcacctgc cccttcaacg    480
gggactgccg catcaccaag gacaaccgac gccactgcca ggcctgccgg ctcaaacgct    540
gtgtggacat cggcatgatg aaggagttca ttctgacaga tgaggaagtg cagaggaagc    600
gggagatgat cctgaagcgg aaggaggagg aggccttgaa ggacagtctg cggcccaagc    660
tgtctgagga gcagcagcgc atcattgcca tactgctgga cgcccaccat aagacctacg    720
accccaccta ctccgacttc tgccagttcc ggcctccagt tcgtgtgaat gatggtggag    780
ggagccatcc ttccaggccc aactccagac acactcccag cttctctggg gactcctcct    840
cctcctgctc agatcactgt atcacctctt cagacatgat ggactcgtcc agcttctcca    900
atctggatct gagtgaagaa gattcagatg acccttctgt gaccctagag ctgtcccagc    960
tctccatgct gccccacctg gctgacctgg tcagttacag catccaaaag gtcattggct   1020
ttgctaagat gataccagga ttcagagacc tcacctctga ggaccagatc gtactgctga   1080
agtcaagtgc cattgaggtc atcatgttgc gctccaatga gtccttcacc atggacgaca   1140
tgtcctggac ctgtgcaaac caagactaca gtaccgcgt cagtgacgtg accaaagccg   1200
gacacagcct ggagctgatt gagcccctca tcaagttcca ggtgggactg aagaagctga   1260
acttgcatga ggaggagcat gtcctgctca tggccatctg catcgtctcc ccagatcgtc   1320
ctggggtgca ggacgccgcg ctgattgagg ccatccagga ccgcctgtcc aacacactgc   1380
agacgtacat ccgctgccgc cacccgcccc gggcagcca cctgctctat gccaagatga   1440
tccagaagct agccgacctg cgcagcctca atgaggagca ctccaagcag taccgctgcc   1500
tctccttcca gcctgagtgc agcatgaagc taacgcccct tgtgctcgaa gtgtttggca   1560
atgagatctc ctga                                                    1574

<210> SEQ ID NO 8
<211> LENGTH: 122
<212> TYPE: DNA
<213> ORGANISM: Homo sapiens

<400> SEQUENCE: 8
ggctcctgaa cctagcccag ctggacggag aaatggactc tagcctcctc tgatagcctc     60
atgccaggcc ccgtgcacat tgctttgctt gcctccctca atcctcatag cttctctttg    120
gg                                                                   122

<210> SEQ ID NO 9
<211> LENGTH: 477
<212> TYPE: PRT
<213> ORGANISM: Homo sapiens

<400> SEQUENCE: 9

Met Glu Trp Arg Asn Lys Lys Arg Ser Asp Trp Leu Ser Met Val Leu
1               5                   10                  15

Arg Thr Ala Gly Val Glu Glu Ala Phe Gly Ser Glu Val Ser Val Arg
            20                  25                  30

Pro His Arg Arg Ala Pro Leu Gly Ser Thr Tyr Leu Pro Pro Ala Pro
        35                  40                  45

Ser Gly Met Glu Ala Met Ala Ala Ser Thr Ser Leu Pro Asp Pro Gly
    50                  55                  60
```

-continued

```
Asp Phe Asp Arg Asn Val Pro Arg Ile Cys Gly Val Cys Gly Asp Arg
 65                  70                  75                  80

Ala Thr Gly Phe His Phe Asn Ala Met Thr Cys Glu Gly Cys Lys Gly
                     85                  90                  95

Phe Phe Arg Arg Ser Met Lys Arg Lys Ala Leu Phe Thr Cys Pro Phe
                100                 105                 110

Asn Gly Asp Cys Arg Ile Thr Lys Asp Asn Arg Arg His Cys Gln Ala
                115                 120                 125

Cys Arg Leu Lys Arg Cys Val Asp Ile Gly Met Met Lys Glu Phe Ile
            130                 135                 140

Leu Thr Asp Glu Glu Val Gln Arg Lys Arg Glu Met Ile Leu Lys Arg
145                 150                 155                 160

Lys Glu Glu Glu Ala Leu Lys Asp Ser Leu Arg Pro Lys Leu Ser Glu
                165                 170                 175

Glu Gln Gln Arg Ile Ile Ala Ile Leu Leu Asp Ala His His Lys Thr
                180                 185                 190

Tyr Asp Pro Thr Tyr Ser Asp Phe Cys Gln Phe Arg Pro Pro Val Arg
                195                 200                 205

Val Asn Asp Gly Gly Ser His Pro Ser Arg Pro Asn Ser Arg His
210                 215                 220

Thr Pro Ser Phe Ser Gly Asp Ser Ser Ser Cys Ser Asp His Cys
225                 230                 235                 240

Ile Thr Ser Ser Asp Met Met Asp Ser Ser Phe Ser Asn Leu Asp
                245                 250                 255

Leu Ser Glu Glu Asp Ser Asp Pro Ser Val Thr Leu Glu Leu Ser
                260                 265                 270

Gln Leu Ser Met Leu Pro His Leu Ala Asp Leu Val Ser Tyr Ser Ile
                275                 280                 285

Gln Lys Val Ile Gly Phe Ala Lys Met Ile Pro Gly Phe Arg Asp Leu
                290                 295                 300

Thr Ser Glu Asp Gln Ile Val Leu Leu Lys Ser Ser Ala Ile Glu Val
305                 310                 315                 320

Ile Met Leu Arg Ser Asn Glu Ser Phe Thr Met Asp Asp Met Ser Trp
                325                 330                 335

Thr Cys Gly Asn Gln Asp Tyr Lys Tyr Arg Val Ser Asp Val Thr Lys
                340                 345                 350

Ala Gly His Ser Leu Glu Leu Ile Glu Pro Leu Ile Lys Phe Gln Val
                355                 360                 365

Gly Leu Lys Lys Leu Asn Leu His Glu Glu Glu His Val Leu Leu Met
                370                 375                 380

Ala Ile Cys Ile Val Ser Pro Asp Arg Pro Gly Val Gln Asp Ala Ala
385                 390                 395                 400

Leu Ile Glu Ala Ile Gln Asp Arg Leu Ser Asn Thr Leu Gln Thr Tyr
                405                 410                 415

Ile Arg Cys Arg His Pro Pro Gly Ser His Leu Leu Tyr Ala Lys
                420                 425                 430

Met Ile Gln Lys Leu Ala Asp Leu Arg Ser Leu Asn Glu His Ser
                435                 440                 445

Lys Gln Tyr Arg Cys Leu Ser Phe Gln Pro Glu Cys Ser Met Lys Leu
                450                 455                 460

Thr Pro Leu Val Leu Glu Val Phe Gly Asn Glu Ile Ser
465                 470                 475
```

```
<210> SEQ ID NO 10
<211> LENGTH: 450
<212> TYPE: PRT
<213> ORGANISM: Homo sapiens

<400> SEQUENCE: 10

Met Glu Trp Arg Asn Lys Lys Arg Ser Asp Trp Leu Ser Met Val Leu
 1               5                  10                  15

Arg Thr Ala Gly Val Glu Gly Met Glu Ala Met Ala Ala Ser Thr Ser
                20                  25                  30

Leu Pro Asp Pro Gly Asp Phe Asp Arg Asn Val Pro Arg Ile Cys Gly
            35                  40                  45

Val Cys Gly Asp Arg Ala Thr Gly Phe His Phe Asn Ala Met Thr Cys
        50                  55                  60

Glu Gly Cys Lys Gly Phe Phe Arg Arg Ser Met Lys Arg Lys Ala Leu
65                  70                  75                  80

Phe Thr Cys Pro Phe Asn Gly Asp Cys Arg Ile Thr Lys Asp Asn Arg
                85                  90                  95

Arg His Cys Gln Ala Cys Arg Leu Lys Arg Cys Val Asp Ile Gly Met
            100                 105                 110

Met Lys Glu Phe Ile Leu Thr Asp Glu Glu Val Gln Arg Lys Arg Glu
        115                 120                 125

Met Ile Leu Lys Arg Lys Glu Glu Ala Leu Lys Asp Ser Leu Arg
        130                 135                 140

Pro Lys Leu Ser Glu Glu Gln Gln Arg Ile Ile Ala Ile Leu Leu Asp
145                 150                 155                 160

Ala His His Lys Thr Tyr Asp Pro Thr Tyr Ser Asp Phe Cys Gln Phe
                165                 170                 175

Arg Pro Pro Val Arg Val Asn Asp Gly Gly Ser His Pro Ser Arg
            180                 185                 190

Pro Asn Ser Arg His Thr Pro Ser Phe Ser Gly Asp Ser Ser Ser Ser
        195                 200                 205

Cys Ser Asp His Cys Ile Thr Ser Ser Asp Met Met Asp Ser Ser Ser
210                 215                 220

Phe Ser Asn Leu Asp Leu Ser Glu Glu Asp Ser Asp Pro Ser Val
225                 230                 235                 240

Thr Leu Glu Leu Ser Gln Leu Ser Met Leu Pro His Leu Ala Asp Leu
                245                 250                 255

Val Ser Tyr Ser Ile Gln Lys Val Ile Gly Phe Ala Lys Met Ile Pro
            260                 265                 270

Gly Phe Arg Asp Leu Thr Ser Glu Asp Gln Ile Val Leu Leu Lys Ser
        275                 280                 285

Ser Ala Ile Glu Val Ile Met Leu Arg Ser Asn Glu Ser Phe Thr Met
        290                 295                 300

Asp Asp Met Ser Trp Thr Cys Gly Asn Gln Asp Tyr Lys Tyr Arg Val
305                 310                 315                 320

Ser Asp Val Thr Lys Ala Gly His Ser Leu Glu Leu Ile Glu Pro Leu
                325                 330                 335

Ile Lys Phe Gln Val Gly Leu Lys Lys Leu Asn Leu His Glu Glu Glu
            340                 345                 350

His Val Leu Leu Met Ala Ile Cys Ile Val Ser Pro Asp Arg Pro Gly
        355                 360                 365

Val Gln Asp Ala Ala Leu Ile Glu Ala Ile Gln Asp Arg Leu Ser Asn
    370                 375                 380
```

```
Thr Leu Gln Thr Tyr Ile Arg Cys Arg His Pro Pro Gly Ser His
385                 390                 395                 400

Leu Leu Tyr Ala Lys Met Ile Gln Lys Leu Ala Asp Leu Arg Ser Leu
            405                 410                 415

Asn Glu Glu His Ser Lys Gln Tyr Arg Cys Leu Ser Phe Gln Pro Glu
        420                 425                 430

Cys Ser Met Lys Leu Thr Pro Leu Val Leu Glu Val Phe Gly Asn Glu
        435                 440                 445

Ile Ser
    450

<210> SEQ ID NO 11
<211> LENGTH: 72
<212> TYPE: PRT
<213> ORGANISM: Homo sapiens

<400> SEQUENCE: 11

Met Glu Trp Arg Asn Lys Lys Arg Ser Asp Trp Leu Ser Met Val Leu
1               5                   10                  15

Arg Thr Ala Gly Val Glu Gly Met Glu Ala Met Ala Ala Ser Thr Ser
            20                  25                  30

Leu Pro Asp Pro Gly Asp Phe Asp Arg Asn Val Pro Arg Ile Cys Gly
        35                  40                  45

Val Cys Gly Asp Arg Ala Thr Gly Phe His Phe Asn Ala Met Thr Cys
    50                  55                  60

Glu Gly Cys Lys Gly Phe Phe Arg
65                  70

<210> SEQ ID NO 12
<211> LENGTH: 427
<212> TYPE: PRT
<213> ORGANISM: Homo sapiens

<400> SEQUENCE: 12

Met Glu Ala Met Ala Ala Ser Thr Ser Leu Pro Asp Pro Gly Asp Phe
1               5                   10                  15

Asp Arg Asn Val Pro Arg Ile Cys Gly Val Cys Gly Asp Arg Ala Thr
            20                  25                  30

Gly Phe His Phe Asn Ala Met Thr Cys Glu Gly Cys Lys Gly Phe Phe
        35                  40                  45

Arg Arg Ser Met Lys Arg Lys Ala Leu Phe Thr Cys Pro Phe Asn Gly
    50                  55                  60

Asp Cys Arg Ile Thr Lys Asp Asn Arg Arg His Cys Gln Ala Cys Arg
65                  70                  75                  80

Leu Lys Arg Cys Val Asp Ile Gly Met Met Lys Glu Phe Ile Leu Thr
            85                  90                  95

Asp Glu Glu Val Gln Arg Lys Arg Glu Met Ile Leu Lys Arg Lys Glu
        100                 105                 110

Glu Glu Ala Leu Lys Asp Ser Leu Arg Pro Lys Leu Ser Glu Glu Gln
        115                 120                 125

Gln Arg Ile Ile Ala Ile Leu Leu Asp Ala His His Lys Thr Tyr Asp
    130                 135                 140

Pro Thr Tyr Ser Asp Phe Cys Gln Phe Arg Pro Pro Val Arg Val Asn
145                 150                 155                 160

Asp Gly Gly Gly Ser His Pro Ser Arg Pro Asn Ser Arg His Thr Pro
            165                 170                 175
```

```
Ser Phe Ser Gly Asp Ser Ser Ser Cys Ser Asp His Cys Ile Thr
            180                 185                 190

Ser Ser Asp Met Met Asp Ser Ser Phe Ser Asn Leu Asp Leu Ser
        195                 200                 205

Glu Glu Asp Ser Asp Pro Ser Val Thr Leu Glu Leu Ser Gln Leu
    210                 215                 220

Ser Met Leu Pro His Leu Ala Asp Leu Val Ser Tyr Ser Ile Gln Lys
225                 230                 235                 240

Val Ile Gly Phe Ala Lys Met Ile Pro Gly Phe Arg Asp Leu Thr Ser
                245                 250                 255

Glu Asp Gln Ile Val Leu Leu Lys Ser Ser Ala Ile Glu Val Ile Met
            260                 265                 270

Leu Arg Ser Asn Glu Ser Phe Thr Met Asp Asp Met Ser Trp Thr Cys
                275                 280                 285

Gly Asn Gln Asp Tyr Lys Tyr Arg Val Ser Asp Val Thr Lys Ala Gly
            290                 295                 300

His Ser Leu Glu Leu Ile Glu Pro Leu Ile Lys Phe Gln Val Gly Leu
305                 310                 315                 320

Lys Lys Leu Asn Leu His Glu Glu Glu His Val Leu Leu Met Ala Ile
                325                 330                 335

Cys Ile Val Ser Pro Asp Arg Pro Gly Val Gln Asp Ala Ala Leu Ile
                340                 345                 350

Glu Ala Ile Gln Asp Arg Leu Ser Asn Thr Leu Gln Thr Tyr Ile Arg
            355                 360                 365

Cys Arg His Pro Pro Gly Ser His Leu Leu Tyr Ala Lys Met Ile
            370                 375                 380

Gln Lys Leu Ala Asp Leu Arg Ser Leu Asn Glu Glu His Ser Lys Gln
385                 390                 395                 400

Tyr Arg Cys Leu Ser Phe Gln Pro Glu Cys Ser Met Lys Leu Thr Pro
                405                 410                 415

Leu Val Leu Glu Val Phe Gly Asn Glu Ile Ser
            420                 425
```

<210> SEQ ID NO 13
<211> LENGTH: 142
<212> TYPE: DNA
<213> ORGANISM: Homo sapiens

<400> SEQUENCE: 13
atcccttaag ggctcctgaa cctagcccag ctggacggag aaatggactc tagcctcctc    60
tgatagcctc atgccaggcc ccgtgcacat tgctttgctt gcctccctca atcctcatag   120
ctcctctttg gggtaagtac ag                                            142

<210> SEQ ID NO 14
<211> LENGTH: 26
<212> TYPE: PRT
<213> ORGANISM: Homo sapiens

<400> SEQUENCE: 14

```
Met Glu Ala Met Ala Ala Ser Thr Ser Leu Pro Asp Pro Gly Asp Phe
1               5                   10                  15

Asp Arg Asn Val Pro Arg Ile Asp Asx Asp
            20                  25
```

<210> SEQ ID NO 15
<211> LENGTH: 76

```
<212> TYPE: PRT
<213> ORGANISM: Homo sapiens

<400> SEQUENCE: 15

Met Glu Trp Arg Asn Lys Lys Arg Ser Asp Trp Leu Ser Met Val Leu
 1               5                  10                  15

Arg Thr Ala Gly Val Glu Glu Ala Phe Gly Ser Glu Val Ser Val Arg
             20                  25                  30

Pro His Arg Arg Ala Pro Leu Gly Ser Thr Tyr Leu Pro Pro Ala Pro
         35                  40                  45

Ser Gly Met Glu Ala Met Ala Ala Ser Thr Ser Leu Pro Asp Pro Gly
     50                  55                  60

Asp Phe Asp Arg Asn Val Pro Arg Ile Asp Asx Asp
 65                  70                  75

<210> SEQ ID NO 16
<211> LENGTH: 49
<212> TYPE: PRT
<213> ORGANISM: Homo sapiens

<400> SEQUENCE: 16

Met Glu Trp Arg Asn Lys Lys Arg Ser Asp Trp Leu Ser Met Val Leu
 1               5                  10                  15

Arg Thr Ala Gly Val Glu Gly Met Glu Ala Met Ala Ala Ser Thr Ser
             20                  25                  30

Leu Pro Asp Pro Gly Asp Phe Asp Arg Asn Val Pro Arg Ile Asp Asx
         35                  40                  45

Asp

<210> SEQ ID NO 17
<211> LENGTH: 1463
<212> TYPE: DNA
<213> ORGANISM: Homo sapiens

<400> SEQUENCE: 17
caaaggaaga agacagcccc gcggaaccgt acctcacctc cttattcttt tcctcgctaa      60
ccgacagcta ccacgagtct tgacgacctc acctccttcg ctttgggtct gaagtgtctg     120
tgagacctca cagaagagca cccctgggct ggtgaatgga cggggacga ggaagtccct      180
acctccgtta ccgccggtcg tgaagggacg gactgggacc tctgaaactg gccttgcacg     240
gggcctagac accccacaca cctctggctc ggtgaccgaa agtgaagtta cgatactgga     300
cacttccgac gtttccgaag aagtccgctt cgtacttcgc cttccgtgat aagtggacgg     360
ggaagttgcc cctgacggcg tagtggttcc tgttggctgc ggtgacggtc cggacggccg     420
agtttgcgac acacctgtag ccgtactact cctcaagta agactgtcta ctccttcacg     480
tctccttcgc cctctactag gacttcgcct tcctcctcct ccggaacttc ctgtcagacg     540
ccgggttcga cagactcctc gtcgtcgcgt agtaacggta tgacgacctg cgggtggtat     600
tctggatgct ggggtggatg aggctgaaga cggtcaaggc cggaggtcaa gcacacttac     660
taccacctcc ctcggtagga aggtccgggt tgaggtctgt gtgagggtcg aagagacccc     720
tgaggaggag gaggacgagt ctagtgacat agtggagaag tctgtactac ctgagcaggt     780
cgaagaggtt agacctagac tcacttcttc taagtctact gggaagacac tgggatctcg     840
acagggtcga gaggtacgac ggggtggacc gactggacca gtcaatgtcg taggttttcc     900
agtaaccgaa acgattctac tatggtccta agtctctgga gtggagactc ctggtctagc     960
```

```
atgacgactt cagttcacgg taactccagt agtacaacgc gaggttactc aggaagtggt    1020
acctgctgta caggacctgg acaccgttgg ttctgatgtt catggcgcag tcactgcact    1080
ggtttcggcc tgtgtcggac ctcgactaac tcggggagta gttcaaggtc caccctgact    1140
tcttcgactt gaacgtactc ctcctcgtac aggacgagta ccggtagacg tagcagaggg    1200
gtctagcagg accccacgtc ctgcggcgcg actaactccg gtaggtcctg gcggacaggt    1260
tgtgtgacgt ctgcatgtag gcgacggcgg tgggcggggg cccgtcggtg gacgagatac    1320
ggttctacta ggtcttcgat cggctggacg cgtcggagtt actcctcgtg aggttcgtca    1380
tggcgacgga gaggaaggtc ggactcacgt cgtacttcga ttgcggggaa cacgagcttc    1440
acaaaccgtt actctagagg act                                           1463

<210> SEQ ID NO 18
<211> LENGTH: 1382
<212> TYPE: DNA
<213> ORGANISM: Homo sapiens

<400> SEQUENCE: 18
caaaggaaga agacagcccc gcggaaccgt acctcacctc cttattcttt tcctcgctaa      60
ccgacagcta ccacgagtct tgacgacctc acctccccta cctccgttac cgccggtcgt     120
gaagggacgg actgggacct ctgaaactgg ccttgcacgg ggcctagaca ccccacacac     180
ctctggctcg gtgaccgaaa gtgaagttac gatactggac acttccgacg tttccgaaga     240
agtccgcttc gtacttcgcc ttccgtgata agtggacggg gaagttgccc ctgacggcgt     300
agtggttcct gttggctgcg gtgacggtcc ggacggccga gtttgcgaca cacctgtagc     360
cgtactactt cctcaagtaa gactgtctac tccttcacgt ctccttcgcc ctctactagg     420
acttcgcctt cctcctcctc cggaacttcc tgtcagacgc cgggttcgac agactcctcg     480
tcgtcgcgta gtaacggtat gacgacctgc gggtggtatt ctggatgctg ggtggatga     540 ggctgaagac ggtcaaggcc ggaggtcaag cacacttact accacctccc tcggtaggaa     600
ggtccgggtt gaggtctgtg tgaggtcgga gagacccct gaggaggagg aggacgagtc     660
tagtgacata gtggagaagt ctgtactacc tgagcaggtc gaagaggtta gacctagact     720
cacttcttct aagtctactg ggaagacact gggatctcga cagggtcgag aggtacgacg     780
gggtggaccg actggaccag tcaatgtcgt aggttttcca gtaaccgaaa cgattctact     840
atggtcctaa gtctctggag tggagactcc tggtctagca tgacgacttc agttcacggt     900
aactccagta gtacaacgcg aggttactca ggaagtggta cctgctgtac aggacctgga     960
caccgttggt tctgatgttc atggcgcagt cactgcactg gtttcggcct gtgtcggacc    1020
tcgactaact cggggagtag ttcaaggtcc accctgactt cttcgacttg aacgtactcc    1080
tcctcgtaca ggacgagtac cggtagacgt agcagagggg tctagcagga ccccacgtcc    1140
tgcggcgcga ctaactccgg taggtcctgg cggacaggtt gtgtgacgtc tgcatgtagg    1200 cgacggcgt gggcgggggc ccgtcggtgg acgagatacg gttctactag gtcttcgatc    1260
ggctggacgc gtcggagtta ctcctcgtga ggttcgtcat ggcgacggag aggaaggtcg    1320
gactcacgtc gtacttcgat tgcggggaac acgagcttca caaaccgtta ctctagagga    1380
ct                                                                 1382

<210> SEQ ID NO 19
<211> LENGTH: 1534
<212> TYPE: DNA
<213> ORGANISM: Homo sapiens
```

-continued

<400> SEQUENCE: 19

```
caaaggaaga agacagcccc gcggaaccgt acctcacctc cttattcttt tcctcgctaa      60
ccgacagcta ccacgagtct tgacgacctc acctcccta cctccgttac cgccggtcgt     120
gaagggacgg actgggacct ctgaaactgg ccttgcacgg ggcctagaca ccccacacac     180
ctctggctcg gtgaccgaaa gtgaagttac gatactggac acttccgacg tttccgaaga     240
agtccactcg gggggagggt ccgagagggg tcacctttcc ctccctcttc ttcgttccac     300
aaaggtactt ccctcgggaa cgtaaaaagt gtagaggaag gaatgttaca ggtaccttgt     360
acgccgcgag tgtcggtgtc ctcgtcctcc cagaaccgct tcgtacttcg ccttccgtga     420
taagtggacg gggaagttgc ccctgacggc gtagtggttc ctgttggctg cggtgacggt     480
ccggacggcc gagtttgcga cacacctgta gccgtactac ttcctcaagt aagactgtct     540
actccttcac gtctccttcg ccctctacta ggacttcgcc ttcctcctcc tccggaactt     600
cctgtcagac gccgggttcg acagactcct cgtcgtcgcg tagtaacggt atgacgacct     660
gcgggtggta ttctggatgc tggggtggat gaggctgaag acggtcaagg ccggaggtca     720
agcacactta ctaccacctc cctcggtagg aaggtccggg ttgaggtctg tgtgagggtc     780
gaagagaccc ctgaggagga ggaggacgag tctagtgaca tagtggagaa gtctgtacta     840
cctgagcagg tcgaagaggt tagacctaga ctcacttctt ctaagtctac tgggaagaca     900
ctgggatctc gacagggtcg agaggtacga cggggtggac cgactggacc agtcaatgtc     960
gtaggttttc cagtaaccga aacgattcta ctatggtcct aagtctctgg agtggagact    1020
cctggtctag catgacgact tcagttcacg gtaactccag tagtacaacg cgaggttact    1080
caggaagtgg tacctgctgt acaggacctg gacaccgttg gttctgatgt tcatggcgca    1140
gtcactgcac tggtttcggc ctgtgtcgga cctcgactaa ctcggggagt agttcaaggt    1200
ccaccctgac ttcttcgact tgaacgtact cctcctcgta caggacgagt accggtagac    1260
gtagcagagg ggtctagcag gaccccacgt cctgcggcgc gactaactcc ggtaggtcct    1320
ggcggacagg ttgtgtgacg tctgcatgta ggcgacggcg gtgggcgggg gcccgtcggt    1380
ggacgagata cggttctact aggtcttcga tcggctggac gcgtcggagt tactcctcgt    1440
gaggttcgtc atggcgacgg agaggaaggt cggactcacg tcgtacttcg attgcgggga    1500
acacgagctt cacaaaccgt tactctagag gact                                1534
```

<210> SEQ ID NO 20
<211> LENGTH: 1574
<212> TYPE: DNA
<213> ORGANISM: Homo sapiens

<400> SEQUENCE: 20

```
acgctggaac cgccactcgg accctgtcc ccactccggt ctctgcctgc ctgcgtcccc      60
gggccgggtt ccgctccctc ttgtcgccgt gattccgtct ttccttctcc cgccacacaa     120
gtgggcgtcg ggttaggtag tgagtcgttg aggatctgcg accatctttc aaggaggctc     180
ctcggacggt aggtcagcac gcacgtcttc ggaaacccag acttcacaga cactctggag     240
tgtcttctcg tggggacccg aggtgaatgg acggggacg aggaagtccc tacctccgtt     300
accgccggtc gtgaagggac ggactgggac ctctgaaact ggccttgcac ggggcctaga     360
caccccacac acctctggct cggtgaccga aagtgaagtt acgatactgg acacttccga     420
cgtttccgaa gaagtccgct tcgtacttcg ccttccgtga taagtggacg gggaagttgc     480
```

-continued

```
ccctgacggc gtagtggttc ctgttggctg cggtgacggt ccggacggcc gagtttgcga      540
cacacctgta gccgtactac ttcctcaagt aagactgtct actccttcac gtctccttcg      600
ccctctacta ggacttcgcc ttcctcctcc tccggaactt cctgtcagac gccgggttcg      660
acagactcct cgtcgtcgcg tagtaacggt atgacgacct gcgggtggta ttctggatgc      720
tggggtggat gaggctgaag acggtcaagg ccggaggtca agcacactta ctaccacctc      780
cctcggtagg aaggtccggg ttgaggtctg tgtgagggtc gaagagaccc ctgaggagga      840
ggaggacgag tctagtgaca tagtggagaa gtctgtacta cctgagcagg tcgaagaggt      900
tagacctaga ctcacttctt ctaagtctac tgggaagaca ctgggatctc gacagggtcg      960
agaggtacga cggggtggac cgactggacc agtcaatgtc gtaggttttc cagtaaccga     1020
aacgattcta ctatggtcct aagtctctgg agtggagact cctggtctag catgacgact     1080
tcagttcacg gtaactccag tagtacaacg cgaggttact caggaagtgg tacctgctgt     1140
acaggacctg gacaccgttg gttctgatgt tcatggcgca gtcactgcac tggtttcggc     1200
ctgtgtcgga cctcgactaa ctcggggagt agttcaaggt ccaccctgac ttcttcgact     1260
tgaacgtact cctcctcgta caggacgagt accggtagac gtagcagagg ggtctagcag     1320
gaccccacgt cctgcggcgc gactaactcc ggtaggtcct ggcggacagg ttgtgtgacg     1380
tctgcatgta ggcgacggcg gtgggcgggg gcccgtcggt ggacgagata cggttctact     1440
aggtcttcga tcggctggac gcgtcggagt tactcctcgt gaggttcgtc atggcgacgg     1500
agaggaaggt cggactcacg tcgtacttcg attgcgggga acacgagctt cacaaaccgt     1560
tactctagag gact                                                       1574

<210> SEQ ID NO 21
<211> LENGTH: 22
<212> TYPE: PRT
<213> ORGANISM: Homo sapiens

<400> SEQUENCE: 21

Met Glu Trp Arg Asn Lys Lys Arg Ser Asp Trp Leu Ser Met Val Leu
  1               5                  10                  15

Arg Thr Ala Gly Val Glu
              20

<210> SEQ ID NO 22
<211> LENGTH: 106
<212> TYPE: DNA
<213> ORGANISM: Homo sapiens

<400> SEQUENCE: 22
gtttccttct tctgtcgggg cgccttggca tggagtggag gaataagaaa aggagcgatt       60
ggctgtcgat ggtgctcaga actgctggag tggagggtgt gtaacc                    106

<210> SEQ ID NO 23
<211> LENGTH: 27
<212> TYPE: DNA
<213> ORGANISM: Homo sapiens

<400> SEQUENCE: 23
ccgcttcatg cttcgcctga agaagcc                                          27

<210> SEQ ID NO 24
<211> LENGTH: 29
<212> TYPE: DNA
<213> ORGANISM: Homo Sapiens
```

```
<400> SEQUENCE: 24
tgcagaattc acaggtcata gcattgaag                                            29

<210> SEQ ID NO 25
<211> LENGTH: 22
<212> TYPE: DNA
<213> ORGANISM: Homo sapiens

<400> SEQUENCE: 25
ggctgtcgat ggtgctcaga ac                                                   22

<210> SEQ ID NO 26
<211> LENGTH: 22
<212> TYPE: DNA
<213> ORGANISM: Homo sapiens

<400> SEQUENCE: 26
aagttcctcc gaggagcctg cc                                                   22

<210> SEQ ID NO 27
<211> LENGTH: 5
<212> TYPE: PRT
<213> ORGANISM: Homo sapiens

<400> SEQUENCE: 27

Arg Asn Lys Lys Arg
 1               5

<210> SEQ ID NO 28
<211> LENGTH: 5
<212> TYPE: PRT
<213> ORGANISM: Homo sapiens

<400> SEQUENCE: 28

Arg Pro His Arg Arg
 1               5
```